United States Patent [19]

Honma et al.

[11] Patent Number: 5,002,945
[45] Date of Patent: Mar. 26, 1991

[54] IMIDAZOLE DERIVATIVES

[75] Inventors: Yasushi Honma, Ageo; Hajime Tamaki, Sakado; Tetsuo Magaribuchi, Urawa; Mine Takido, Tokyo, all of Japan

[73] Assignee: Tanabe Seiyaku Co. Ltd., Osaka, Japan

[21] Appl. No.: 364,999

[22] Filed: Jun. 9, 1989

Related U.S. Application Data

[62] Division of Ser. No. 122,286, Nov. 18, 1987, abandoned.

[30] Foreign Application Priority Data

Dec. 2, 1986 [JP] Japan .................................. 61-287512
Mar. 31, 1987 [JP] Japan .................................. 62-80475
Aug. 28, 1987 [JP] Japan .................................. 62-215813

[51] Int. Cl.$^5$ .................... C07D 413/14; A61K 31/44
[52] U.S. Cl. .................... 514/231.5; 514/318; 514/338; 514/341; 514/339; 546/271; 546/194; 546/278; 546/281; 546/272; 544/131; 544/124
[58] Field of Search ............... 546/271, 194; 544/131, 544/124; 514/338, 318, 228

[56] References Cited

U.S. PATENT DOCUMENTS 4,255,431  3/1981  Junggren et al. .................... 546/271

FOREIGN PATENT DOCUMENTS 0001279   4/1979  European Pat. Off. .
20004648 10/1979  European Pat. Off. .
0125756 11/1984  European Pat. Off. .
0167943  1/1986  European Pat. Off. .
0174717  3/1986  European Pat. Off. .
0176308  4/1986  European Pat. Off. .

OTHER PUBLICATIONS

Chemical Abstract 93, 107008f, 1980.
Chemical Abstract 80, 420p, 1974.
Chemical Abstract 88, 115087t, 1978.
Chemical Abstract 103, 6306w, 1985.

Primary Examiner—Jane T. Fan
Attorney, Agent, or Firm—Browdy and Neimark

[57] ABSTRACT

Novel imidazole of the formula:

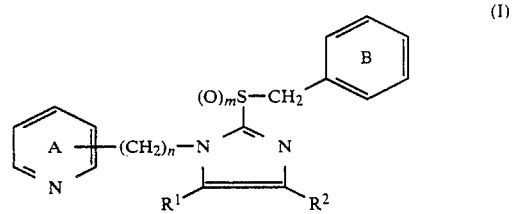

wherein Ring A is pyridyl group or a substituted pyridyl group; Ring B is phenyl group or a substituted phenyl group; $R^1$ and $R^2$ are hydrogen atom or are combined together to form a group of the formula: $-(CH_2)_q-$; m is 1 or 2; n is 0, 1 or 2; and q is 3 or 4, or a salt thereof are disclosed. Said derivative (I) and a salt thereof are useful as anti-ulcer agents.

21 Claims, No Drawings

IMIDAZOLE DERIVATIVES

This is a divisional of copending application Ser. No. 122,286, filed on Nov. 18, 1987 now abandoned.

This invention relates to a novel imidazole derivative and processes for preparing same. More particularly, it relates to an imidazole derivative of the formula:

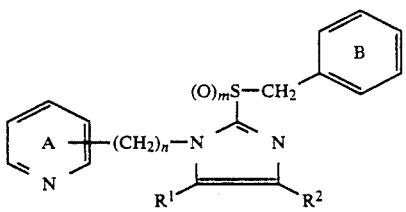

wherein Ring A is pyridyl group or a substituted pyridyl group, Ring B is phenyl group or a substituted phenyl group; $R^1$ and $R^2$ are hydrogen atom or are combined together to form a group of the formula: —$(CH_2)_q$13; m is 1 or 2; n is 0, 1 or 2; and q is 3 or 4, or a salt thereof.

Excessive gastric acid secretion is one of causative factors of peptic ulcer diseases such as gastric ulcer and duodenal ulcer. Since the acid secretion by gastric parietal cells is known to be induced by histamine, acetylcholine or gastrin, cholinergic receptor blockers (e.g., atropine) and histamine $H_2$-receptor blockers (e.g., cimetidine) which antagonize these stimuli in living tissues have been used for treatment of such ulcer diseases [Medicina, 23(4) 560–565 (1986)].

Moreover, benzimidazole compounds such as omeprazole have been recently found to show the antisecretory effects due to their inhibitory effect on the enzymatic activity of $H^+/K^+$ ATPase (i.e., the enzyme which plays an important role in concentration and/or secretion of gastric acid) (Japanese Patent Publication (unexamined) No. 141783/1979).

However, among these known drugs, cholinergic receptor blockers are still unsatisfactory for clinical use because of strong toxicity (e.g., atropine toxicosis). Cimetidine, one of the histamine $H_2$ receptor blockers, is also known to have unfavorable side effects such as anti-androgen effect and prolactin release-stimulating effect.

As a result of various investigations, we have now found that the compound (I) of the present invention and a salt thereof show potent inhibitory effect against gastric acid secretion and is useful for therapeutic treatment or prophylaxis of peptic ulcer diseases. For example, when the effect of a test compound on gastrin-induced gastric acid secretion was examined by oral administration to rats, each one of 1-(2-pyridyl)-2-[2-(1-pyrrolyl)benzylsulfinyl]imidazole, 1-(3-methyl-2-pyridyl)-2-[2-(dimethylamino)benzylsulfinyl]imidazole and 1,4,5,6-tetrahydro-1-(2-pyridyl)-2-[2-(dimethylamino)benzylsulfinyl] cyclopenta[d]imidazole at the dose of 30 mg/kg showed more than 70% decrease in gastric acid secretion as compared with non-administered group of rats. On the other hand, when the effect of a test compound on the enzyme activity of $H^+/K^+$ ATPass prepared from the porcine gastric mucosa was examined, $IC_{50}$ (i.e., the concentration required to induce 50% inhibition of said enzymatic activity) of 1,4,5,6-tetrahydro-1-(2-pyridyl)2-[2-(diethylamino)benzylsulfinyl]cyclopenta[d]imidazole was about 10 $\mu M$ and $IC_{50}$ of 1-(2-pyridyl)-2-[2-(cyclohexylamino)benzylsulfinyl]imidazole and 1-(4-methoxy-6-methyl-2-pyridyl)-2-[2-(diethylamino)benzylsulfinyl]imidazole were less than 10 $\mu M$.

Examples of the compound of the present invention are those of the formula (I) in which Ring A is a 2-, 3- or 4-pyridyl group which may optionally have one or two substituent(s) selected from a halogen atom such as chlorine atom or bromine atom, a lower alkyl group such as methyl group or ethyl group, a lower alkoxy group such as methoxy group, ethoxy group or isopropoxy group, a phenyl-lower alkoxy group such as benzyloxy group, nitro group, amino group, a lower alkanoylamino group such as acetylamino group or propionylamino group, a N-lower alkyl-N-lower alkanoylamino group such as N-methyl-N-acetylamino group, a mono- or di(lower alkyl)amino group such as methylamino group, ethylamino group, dimethylamino group or diethylamino group, a lower alkanoyloxy group such as acetoxy group, cyanide group, a trihalogeno-lower alkyl group such as trifluoromethyl group, a trihalogeno-lower alkoxy group such as 2,2,2-trifluoroethoxy group, a lower alkenyloxy group such as allyloxy group, and hydroxy group; Ring B is a phenyl group which may optionally have one substituent selected from nitro group, amino group, a mono- or di(lower alkyl)amino group such as methylamino group, ethylamino group, dimethylamino group, diethylamino group or dipropylamino group, a lower alkanoylamino group such as acetylamino group or propionylamino group, phenylamino group, a cycloalkylamino group such as cyclohexylamino group, a N-(tri-lower alkylphenyl)sulfonylamino group such as (2,4,6-trimethylphenyl)sulfonylamino group, a N-lower alkyl-N-(tri-lower alkylphenyl)sulfonylamino group such as N-methyl-N-(2,4,6-trimethylphenyl)sulfonylamino group, a N-lower alkyl-N-phenylamino group such as N-methyl-N-phenylamino group or N-ethyl-N-phenylamino group, a di(lower alkyl)amino-lower alkylideneamino group such as dimethylamino-methylideneamino group, a di(lower alkyl)amino-lower alkyl group such as dimethylaminomethyl group or diethylaminomethyl group, a N-lower alkyl-N-lower alkanoylamino group such as N-methyl-N-acetylamino group, a lower alkoxy group such as methoxy group or ethoxy group, an arylcarbonylamino group such as benzoylamino group, a lower alkylsulfonylamino group such as methanesulfonylamino group, formylamino group, a lower alkoxycarbonylamino group such as methoxycarbonylamino group or ethoxycarbonylamino group, phthalimido group and a nitrogen-containing 5- or 6-membered hetero monocyclic group such as morpholino group, imidazolyl group, pyrrolyl group, pyrrolidinyl group or piperidino group; $R^1$ and $R^2$ are hydrogen atom or are combined together to form trimethylene group or tetramethylene group; m is 1 or 2; and n is 0, 1 or 2.

Among them, preferred examples of the compound of the invention are those of the formula (I) in which Ring A is 2- or 4-pyridyl group which may optionally have one or two substituent(s) selected from a $C_{1-4}$ alkyl group, a $C_{1-4}$ alkoxy group and a $C_{7-8}$ phenylalkoxy group; ring B is phenyl group which may optionally have one substituent selected from a di($C_{1-4}$ alkyl)amino group, a $C_{1-4}$ alkanoylamino group, morpholino group, pyrrolyl group and piperidino group; $R^1$ and $R^2$ are hydrogen atom or are combined together to form trimethylene group; m is 1; and n is 0, 1 or 2.

More preferred examples of the compound of the invention are those of the formula (I) in which Ring A is 2- or 4-pyridyl group, a 3-, 4- or 5-($C_{1-4}$ alkoxy)-2-pyridyl group, a 3-, 4-, 5- or 6-($C_{1-4}$ alkyl)-2-pyridyl group, a 3-($C_{7-8}$ phenylalkoxy)-2-pyridyl group, a 2-($C_{1-4}$ alkyl)-4-pyridyl group or a 4-($C_{1-4}$ alkoxy)-6-($C_{1-4}$ alkyl)-2-pyridyl group; Ring B is phenyl group, 2-morpholinophenyl group, a 2-di($C_{1-4}$ alkyl)aminophenyl group, 2-(pyrrolyl)phenyl group, 2-piperidino group or a 2-($C_{1-4}$ alkanoyl)aminophenyl group; $R^1$ and $R^2$ are hydrogen atom or are combined together to form trimethylene group; m is 1; and n is 0, 1 or 2.

Most preferred examples of the compound of the invention are those of the formula (I) in which Ring A is 2-pyridyl group or a 3-($C_{1-4}$ alkyl)-2-pyridyl group; Ring B is phenyl group, a 2-($C_{1-4}$ alkyl)aminophenyl group or 2-(1-pyrrolyl)phenyl group, $R^1$ and $R^2$ are hydrogen atom or are combined together to form trimethylene group; m is 1; and n is 0.

While the compound (I) of the present invention in which m is 1 may exist in the form of two optically active isomers due to an asymmetric sulfoxide group, the present invention includes within its scope either one of these isomers and a mixture thereof.

According to the present invention, the compound (I) or a salt thereof can be prepared by the steps of:

(i) condensing a mercaptoimidazole compound of the formula:

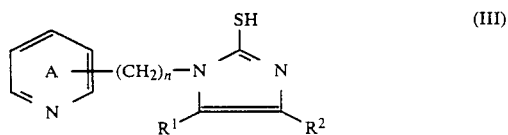

wherein Ring A, $R^1$, $R^2$ and n are the same as defined above, or a salt thereof with a toluene compound of the formula:

wherein X is a reactive residue and Ring B is the same as defined above, or a salt thereof, (ii) oxidizing the resultant product of the formula:

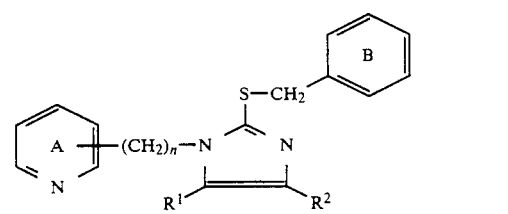

wherein Ring A, Ring B, $R^1$, $R^2$ and n are the same as defined above, and (iii) if required, further converting the product into a salt thereof.

Alternatively, the compound (I) in which $R^1$ and $R^2$ are combined together to form a group of the formula: —$(CH_2)_q$— (wherein q is the same as defined above) or a salt thereof can be prepared by the steps of:

(iv) dehydrating a compound of the formula:

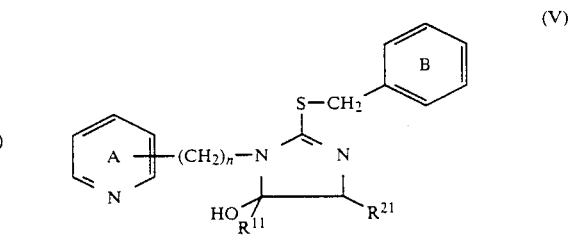

wherein $R^{11}$ and $R^{21}$ are combined together to form a group of the formula: —$(CH_2)_q$— and Ring A, Ring B, q and n are the same as defined above, (v) oxidizing the resultant product, and (vi) if required, further converting the product into a salt thereof.

The condensation of the mercaptoimidazole compound (III) and the toluene compound (IV) can be conducted in the presence or absence of an acid acceptor in an inert solvent. Any groups which enable to form C—S bond through reaction with a mercapto group can be used as the reactive residue "X" of the toluene compound (IV). Such reactive residue X includes, for example, a halogen atom, an alkylsulfonyloxy group (e.g., methylsulfonyloxy group), an arylsulfonyloxy group (e.g., toluenesulfonyloxy group, benzenesulfonyloxy group) and the like. The compound (IV) which has amino group, a N-substituted amino group and the like on the benzene ring may, if required, be used for the reaction in the form of an organic or inorganic acid addition salt such as hydrochloride, hydrobromide, sulfate, nitrate, formate, oxalate or methanesulfonate. On the other hand, the compound (III) may, if required, be used for the reaction in the form of an organic or inorganic acid addition salt (e.g., hydrochloride, hydrobromide, sulfate, nitrate, formate, oxalate or methanesulfonate), an alkali metal salt (e.g., sodium salt or potassium salt), an alkaline earth metal salt (e.g., calcium salt or magnesium salt), and a quaternary ammonium salt (e.g., tetramethylammonium salt). A lower alkanol, dimethylformamide, dimethylsulfoxide, water and the mixture thereof are suitable as the solvent. Suitable examples of the acid acceptor include inorganic bases such as an alkali metal hydroxide, an alkali earth metal hydroxide, an alkali metal carbonate, an alkali metal bicarbonate, an alkali metal alkoxide, an alkali metal amide, an alkali metal fluoride, an alkali metal hydride, or organic bases such as pyridine, a tri-lower alkylamine, a lower alkyl lithium, a quaternary ammonium hydroxide (e.g., tetra n-butyl ammonium hydroxide), and the like. It is preferred to carry out the reaction at $-20°$ C. to $170°$ C., especially $-10°$ to $100°$ C.

On the other hand, the dehydration of the imidazole derivative (V) can be conducted in the presence of a dehydrating agent in an inert solvent. Suitable examples of the dehydrating agent include organic acids such as formic acid, trifluoroacetic acid, p-toluenesulfonic acid, benzenesulfonic acid or camphorsulfonic acid, mineral acids such as hydrochloric acid or sulfonic acid or a mixture of a halogenating agent (e.g., phosphrus tribromide, phosphorus trichloride or phosphorus oxychloride) and a base (e.g., pyridine or tiethylamine) and the like. The compound (V) may, if required, be used for the reaction in the form of an organic or inorganic acid addition salt such as hydrochloride, hydrobromide, sulfate, nitrate, formate, oxalate or methanesulfonate. It is preferred to carry out the reaction at −20° C. to 150° C., especially −10° C. to 100° C.

The oxidation of the above-obtained compound (II) [including the dehydration product of the imidazole derivative (V)] is conducted by treating it with an oxidative agent.

Conventional oxidative agents such as peroxy acids (e.g., m-chloroperbenzoic acid, perbenzoic acid or peracetic acid), an alkali metal hypochlorite, an alkali metal chlorite, an alkali metal periodate, tetra n-butyl ammonium periodate, tert.-butyl hydroperoxide, iodoxybenzene, and the like can be used for the reaction. A lower alkanol, methylene chloride, chloroform, tetrahydrofuran, dioxane, water and the mixture thereof are suitable as the solvent. It is preferred to carry out the reaction at −70° C. to 100° C., especially −50° C. to 20° C. In this reaction, a sulfinyl-imidazole compound (I) (m=1) is obtained by using an equimolar amount or a little excess amount of the oxidative agent, and a sulfonyl-imidazole compound (I) (m=2) is obtained by using not less than two equimolar amount of the oxidative agent.

The intermediate (II) obtained by the above-mentioned reaction is a novel compound, and the substitutent(s) on the Ring A and/or B thereof may be, if required, modified or converted to other substituent(s) before the oxidation step. For example, the compound (II) having amino group on the Ring A and/or B may be obtained by conventional reduction of the compound (II) having nitro group thereon, or by hydrolysis of the corresponding N-phthalimido or N-tri lower alkylphenylsulfonylamido compound (II). Alternatively, the compound (II) having one or two substituent(s) selected from a lower alkanoylamino group, a lower alkylsulfonylamino group, formylamino group, a lower alkylamino group, an arylcarbonylamino group, a lower alkoxycarbonylamino group and a substituted phenylsulfonylamino group on the Ring A and/or B thereof may be obtained by conventional acylation or alkylation of the compound (II) having amino group, an N-alkylamino group or an N-acylamino group on said Ring A and/or B.

Because of the potent inhibitory effect against gastric acid secretion and/or potent inhibitory effect on the enzymatic activity of H+/K+ ATPase, the imidazole compound (I) of the present invention and a salt thereof are useful for therapeutic treatment and/or prophylaxis of peptic ulcer diseases such as gastric ulcer and duodenal ulcer. The imidazole compound (I) and a salt thereof can be used without unfavorable side effects such as anti-androgen or prolactin release-stimulating effects as observed in histamine H$_2$-receptor blockers. Moreover, since the imidazole compound (I) and a salt thereof may include a group of compounds which inhibit effectively the gastric acid secretion without affecting the enzyme activity of H+/K+ ATPase, such compounds may be used as anti-ulcer agents which are different in mechanism of action from the known H+/K+ ATPase inhibitors such as omeprazole.

The compound (I) can be used for pharmaceutical use either in the free form or in the form of a salt thereof. Suitable salts of the compound (I) for pharmaceutical use include, for example, pharmaceutically acceptable salts such as inorganic acid addition salts (e.g., hydrochloride, hydrobromide, hydroiodide, sulfate, nitrate), organic acid addition salts (e.g., formate, oxalate, methanesulfonate, glucuronate), and the like. Such salts may be obtained by treating the free base of the compound (I) with a stoichiometrically equimolar amount of the acid.

The dose of the compound (I) or a salt thereof may vary depending on the age, condition and body weight of patients, the kind and severity of diseases to be treated and administration route, etc, but may usually be about 0.05 to about 50 mg/kg, preferably about 0.1 to about 20 mg/kg, per day.

The compound (I) and a salt thereof may be administered either orally or parenterally. When administrated orally, the pharmaceutical preparation may be in the solid form such as tablets, powders, capsules or suppositories. These preparations may contain pharmaceutical excipient, binder, diluent, disintegrator or lubricant. The pharmaceutical preparation for oral administration may also be in liquid form such as aqueous or oily suspension, solution, sirup or elixir. Moreover, when administered parenterally, the pharmaceutical preparation may be used in the form of injections.

Concomitantly, the starting compound (III) in which R$^1$ and R$^2$ are hydrogen atom may be prepared by the steps of reacting a pyridine compound of the formula:

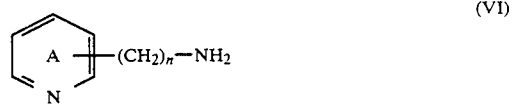

(VI)

wherein Ring A and n are the same as defined above, with a iso (thio) cyanate compound of the formula:

$$Z=C=NCH_2CH(OR^3)_2 \quad (VII)$$

wherein R$^3$ is an alkyl group and Z is oxygen atom or sulfur atom, in an inert solvent, treating the thus-obtained (thio) urea compound with an organic or inorganic acid to give the corresponding cyclic compound, and when Z is oxygen atom, further treating the cyclic compound with a sulfur agent such as Lawesson's Reagent [2,4-bis(4-methoxyphenyl)-1,3-dithia-2,4-diphosphetane-2,4-disulfide], 2,4-diethoxy-1,3-dithia-2,4-diphosphetane-2,4-disulfide or phosphorus pentasulfide. Alternatively, the starting compound (III) in which R$^1$ and R$^2$ are combined together to form a group of the formula: —(CH$_2$)$_l$—, (wherein q is the same as defined above) may be prepared by condensing 2-aminocyclohexanone or 2-aminocyclopentanone with a compound of the formula:

(VIII)

wherein Ring A and n are the same as defined above, in the presence of triethylamine, and dehydrating the product in the same manner as described in the dehydration reaction of the imidazole derivative (V). The starting compound (V) may be prepared by condensing 2-aminocyclohexanone or 2-aminocyclopentanone with the compound (VIII) in the presence of triethylamine, and then condensing the product with the toluene compound (IV).

Practical and presently preferred embodiments of the present invention are illustratively shown in the following Examples.

EXAMPLE 1

(1) 3.0 g of 1-(2-pyridyl)-2-mercaptoimidazole are dissolved in 50 ml of ethanol, and 16.9 ml of a 2N-aqueous sodium hydroxide solution are added thereto under ice-cooling. 3.84 g of m-dimethylaminobenzyl chloride hydrochloride are added to the mixture and stirred at room temperature for 2 hours. After the solvent is distilled off, water is added to the residue, and the mixture is extracted with ethyl acetate. The extract is washed with water, dried and evaporated to remove the solvent. The residue is recrystallized from a mixture of ethyl acetate and n-hexane, whereby 3.95 g of 1-(2-pyridyl)-2-(3-dimethylaminobenzylthio)imidazole are obtained.

Yield 75%.

M.p. 79°–80° C.

(2) A solution of 3.73 g of the product obtained above in 100 ml of methylene chloride is cooled to −40° C. under argon gas atmosphere. 5.32 g of 80% m-chloroperbenzoic acid are added thereto gradually. The mixture is stirred at the same temperature for 1 hour. The reaction mixture is washed with a saturated aqueous sodium bicarbonate solution, dried and evaporated to remove the solvent. The residue is recrystallized from methanol, whereby 1.48 g of 1-(2-pyridyl)-2-(3-dimethylaminobenzylsulfinyl)imidazole are obtained.

Yield 55%.

M.p. 177°–179° C.

EXAMPLES 2 to 25

(1) The corresponding starting compounds are treated in the same manner as described in Example 1-(1) to give the compounds shown in Table 1.

TABLE 1

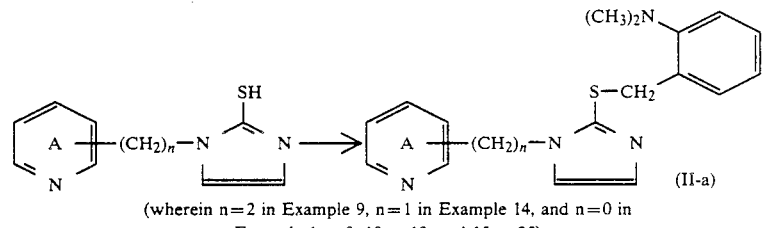

(wherein n=2 in Example 9, n=1 in Example 14, and n=0 in Example 1 to 8, 10 to 13, and 15 to 25)

| Ex. Nos. | Compound (II-a) Ring A | Properties* |
|---|---|---|
| 2-(1) | CF$_3$-pyridyl | M.p. 62 to 64° C. (recrystallized from n-hexane) |
| 3-(1) | 3,4-dimethoxy-pyridyl | oil |
| 4-(1) | 4-OCH$_3$, 2-CH$_3$-pyridyl | oil; NMR, δ: 2.48(s,3H,C—CH$_3$),2.69(s, 6H,N(CH$_3$)$_2$),3.81(s,3H,OCH$_3$),4.58 (s,2H,SCH$_2$) Mass(m/e): 353(M$^+$),134 |
| 5-(1) | 4-OCH$_2$CF$_3$-pyridyl | oil; NMR δ: 2.68(s,6H,N(CH$_3$)$_2$),4.36 (q,2H,OCH$_2$CF$_3$),4.57(s,2H,SCH$_2$) Mass(m/e): 408(M$^+$), 134 |
| 6-(1) | 3-OH-pyridyl | M.p. 158 to 160° C. (recrystallized from methanol, chloroform and isopropyl ether) |
| 7-(1) | CH$_3$-pyridyl | oil |

TABLE 1-continued

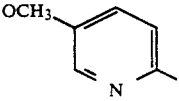

(wherein n=2 in Example 9, n=1 in Example 14, and n=0 in Example 1 to 8, 10 to 13, and 15 to 25)

| Ex. Nos. | Compound (II-a) Ring A | Properties* |
|---|---|---|
| 8-(1) | 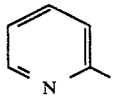 | M.p. 51 to 53.5° C.(recrystallized from ethyl acetate and n-hexane) |
| 9-(1) | 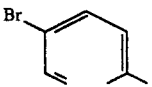 | oil; NMR δ: 2.70(s,6H,N(CH$_3$)$_2$),2.99 (t,2H,J=7Hz,N—CH$_2$),4.20(s,2H,J=7Hz, 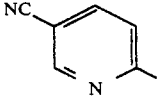 CH$_2$), 4.38(s,2H,SCH$_2$) Mass(m/e): 338(M$^+$), 134 |
| 10-(1) | 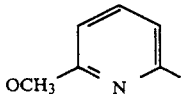 | oil; NMR δ: 2.67(s,6H,N(CH$_3$)$_2$), 4.56(s,2H,SCH$_2$) Mass(m/e): 390,388(M$^+$), 134 |
| 11-(1) | 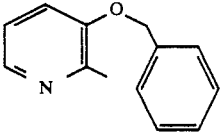 | M.p. 130 to 132° C.(recrystallized from ethanol) |
| 12-(1) | 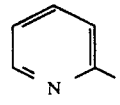 | oil; NMR δ: 2.96(s,6H,N(CH$_3$)$_2$),3.96 (s,3H,OCH$_3$),4.61(s,2H,SCH$_2$) Mass(m/e): 340(M$^+$), 134 |
| 13-(1) | 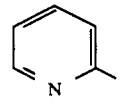 | M.p. 70 to 72° C.(recrystallized from ethyl acetate and isopropyl ether) |
| 14-(1) | 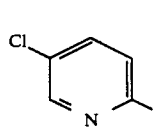 | oil; NMR, δ: 2.66(s,6H,N(CH$_3$)$_2$), 4.38(s,2H,SCH$_2$),5.08(s,2H,NCH$_2$) Mass(m/e): 324(M$^+$) |
| 15-(1) | | oil; NMR, δ: 2.68(s,6H,N(CH$_3$)$_2$), 4.58(s,2H,SCH$_2$) Mass(m/e): 310(M$^+$) |
| 16-(1) | | oil; NMR, δ: 2.67(s,6H,N(CH$_3$)$_2$), 4.56(s,2H,SCH$_2$) Mass(m/e): 344, 346(M$^+$) |

TABLE 1-continued

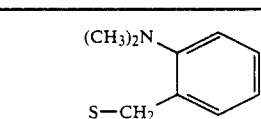

(wherein n=2 in Example 9, n=1 in Example 14, and n=0 in Example 1 to 8, 10 to 13, and 15 to 25)

| Ex. Nos. | Compound (II-a) Ring A | Properties* |
|---|---|---|
| 17-(1) | 5-CH₃, 2-pyridyl | oil; NMR, δ: 2.32(s,3H, 5-CH₃-2-pyridyl), 2.67(s,6H,N(CH₃)₂), 4.57(s,2H,SCH₂) Mass(m/e): 324(M⁺) |
| 18-(1) | 4-pyridyl | oil; NMR, δ: 2.60(s,6H,N(CH₃)₂), 4.45(s,2H,SCH₂) Mass(m/e): 310(M⁺) |
| 19-(1) | 3-pyridyl | oil; NMR, δ: 2.57(s,6H,N(CH₃)₂), 4.38(s,2H,SCH₂) Mass(m/e): 310(M⁺) |
| 20-(1) | 5-NO₂-2-pyridyl | M.p. 140 to 142° C.(recrystallized from chloroform and ethanol) |
| 21-(1) | 4,6-di-CH₃-2-pyridyl | oil; NMR, δ: 2.32(s,3H, 4-CH₃), 2.49(s,3H, 6-CH₃), 2.68(s,6H,N(CH₃)₂), 4.56(s,2H,SCH₂) Mass(m/e): 338(M⁺) |
| 22-(1) | 4-OCH₃-2-pyridyl | oil; NMR, δ: 2.68(s,6H,N(CH₃)₂), 3.85(s,3H,OCH₃), 4.58(s,2H,SCH₂) Mass(m/e): 340(M⁺) |
| 23-(1) | 6-CH₃-2-pyridyl | oil; NMR, δ: 2.54(s,3H, 6-CH₃-2-pyridyl), 2.68(s,6H,N(CH₃)₂), 4.58(s,2H,SCH₂) Mass(m/e): 324(M⁺) |
| 24-(1) | 3-OCH₃-2-pyridyl | oil; NMR,: δ 2.63(s,6H,N(CH₃)₂), 3.81(s,3H,OCH₃), 4.48(s,2H,SCH₂) Mass(m/e): 340(M⁺) |

TABLE 1-continued

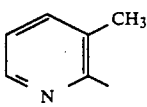

(wherein n=2 in Example 9, n=1 in Example 14, and n=0 in Example 1 to 8, 10 to 13, and 15 to 25)

| Ex. Nos. | Compound (II-a) Ring A | Properties* |
|---|---|---|
| 25-(1) | 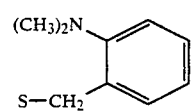 | oil; NMR, δ: 2.08(s,3H,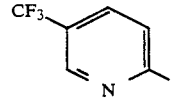), 2.61(s,6H,N(CH$_3$)$_2$), 4.45(s,2H,SCH$_2$) Mass(m/c): 324(M$^+$) |

*note: NMR is measured in CDCl$_3$ (2) The products obtained above are treated in the same manner as described in Example 1-(2) to give the compounds shown in Table 2.

TABLE 2

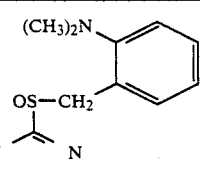

(wherein n=2 in Example 9, n=1 in Example 14, and n=0 in Examples 1 to 8, 10 to 13, and 15 to 25)

| Ex. Nos. | Compound(I-a) Ring A | Properties* |
|---|---|---|
| 2-(2) | 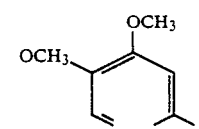 | M.p. 122 to 124.5° C. (recrystallized from ethyl acetate and n-hexane) |
| 3-(2) | 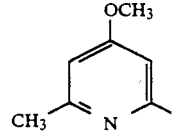 | M.p. 107 to 111° C. (recrystallized from chloroform, isopropyl ether and n-hexane) |
| 4-(2) | 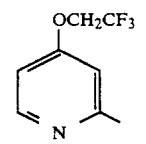 | M.p. 124 to 128° C. (recrystallized from ethyl acetate) |
| 5-(2) | 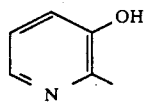 | M.p. 106 to 110° C. (recrystallized from ethyl acetate) |
| 6-(2) | 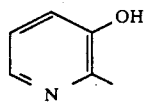 | powder; M.p. about 60° C. NMR, δ: 2.53(s,6H,N(CH$_3$)$_2$), 4.76(ABq,2H,SCH$_2$),9.30(br,1H,OH) Mass(m/e): 342(M$^+$) |

TABLE 2-continued

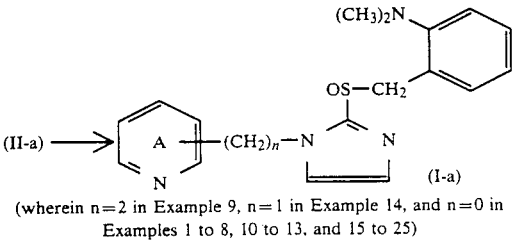

(wherein n=2 in Example 9, n=1 in Example 14, and n=0 in Examples 1 to 8, 10 to 13, and 15 to 25)

| Ex. Nos. | Compound(I-a) Ring A | Properties* |
|---|---|---|
| 7-(2) | CH₃-pyridyl | M.p. 117 to 119° C. (recrystallized from chloroform and isopropyl ether) |
| 8-(2) | OCH₃-pyridyl | M.p. 81.5 to 83.5° C. (recrystallized from ethyl acetate and n-hexane) |
| 9-(2) | pyridyl | oil; NMR, δ: 2.68(s,6H,N(CH₃)₂), 4.82(ABq,2H,SCH₂) IR$\nu_{max}^{liquid}$ (cm⁻¹): 1040 (S—O) Mass(m/e): 339(M⁺ + 1) |
| 10-(2) | Br-pyridyl | M.p. 73 to 75° C. (recrystallized from chloroform and n-hexane) |
| 11-(2) | NC-pyridyl | M.p. 137 to 139° C. (recrystallized from chloroform and n-hexane) |
| 12-(2) | OCH₃-pyridyl | M.p. 102 to 104° C. (recrystallized from ethyl acetate and n-hexane) |
| 13-(2) | benzyloxy-pyridyl | M.p. 95.5 to 97° C. (recrystallized from ethyl acetate and n-hexane) |
| 14-(2) | pyridyl | M.p. 93 to 94° C. (recrystallized from ethyl acetate and ether) |
| 15-(2) | pyridyl | M.p. 104 to 105° C. (recrystallized from ethyl acetate and n-hexane) |
| 16-(2) | Cl-pyridyl | oil; NMR, δ: 2.62(s,6H,N(CH₃)₂), 4.80(ABq,2H,J=12.5Hz, SCH₂) |

TABLE 2-continued

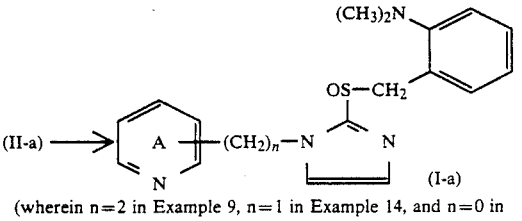

(wherein n=2 in Example 9, n=1 in Example 14, and n=0 in
Examples 1 to 8, 10 to 13, and 15 to 25)

| Ex. Nos. | Compound(I-a) Ring A | Properties* |
|---|---|---|
| 17-(2) | 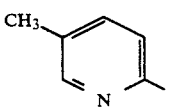 | oil; NMR, δ: 2.38(s,3H,CH₃), 2.63(s,6H,N(CH₃)₂), 4.85(ABq,2H,J=12.5Hz,SCH₂) |
| 18-(2) | 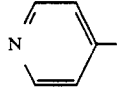 | M.p. 102 to 104° C. (recrystallized from chloroform and isopropyl ether) |
| 19-(2) | 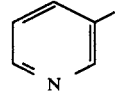 | oil; NMR, δ: 2.55(s,6H,N(CH₃)₂), 4.83(q,2H,J=11.5Hz, SCH₂) Mass(m/e): 326(M⁺) |
| 20-(2) | 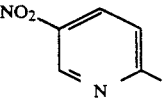 | M.p. 133 to 135° C. (recrystallized from chloroform and isopropyl ether) |
| 21-(2) | 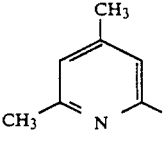 | Oxalate** M.p. 96 to 100° C. (decomp.) |
| 22-(2) | 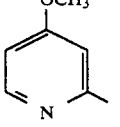 | M.p. 117 to 120° C. (recrystallized from isopropyl alcohol and isopropyl ether) |
| 23-(2) | 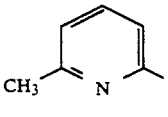 | Oxalate** M.p. 82 to 94° C. (decomp.) |
| 24-(2) | 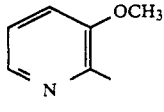 | oil; NMR, δ: 2.61(s,6H,N(CH₃)₂),3.83 (s,3H,OCH₃),4.80(ABq,2H,J=12.5Hz,SCH₂) Mass(m/e): 356(M⁺),134 |
| 25-(2) | 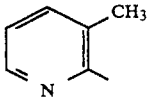 | M.p. 89 to 92° C. (recrystallized from ethyl acetate and n-hexane) NMR, δ: 2.11(s,3H, 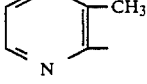 —CH₃), 2.59(s,6H,N(CH₃)₂), 4.80(ABq,2H,J=12.5Hz,SCH₂) |

*note: NMR is measured in CDCl₃

EXAMPLES 26 to 31

(1) The corresponding starting compounds are treated in the same manner as described in Example 1-(1) to give the compounds shown in Table 3.

TABLE 3

[Structure: pyridine ring A with (CH₂)ₙ-N-C(SH)=N in imidazole ring] →

[Structure: pyridine ring A with (CH₂)ₙ-N-C(S-CH₂-C₆H₄-N(C₂H₅)₂)=N in imidazole ring]

(II-b)

(wherein n = 0)

| Ex. Nos. | Compound(II-b) Ring A | Properties |
|---|---|---|
| 26-(1) | 4-CH₃, 2-pyridyl | oil; NMR,δ: 0.95(t,6H,NCH₂CH₃), 2.37(s,3H,C—CH₃),2.95(q,4H, NCH₂CH₃),4.56(s,2H,SCH₂)Mass (m/e: 352(M⁺),146 |
| 27-(1) | 3-CH₃, 2-pyridyl | oil; NMR,δ: 0.87(t,6H,NCH₂CH₃), 2.04(s,3H,C—CH₃),2.88(q,4H, NCH₂CH₃),4.44(s,2H,SCH₂)Mass (m/e: 352(M⁺),146 |
| 28-(1) | 4-OCH₃, 6-CH₃, 2-pyridyl | oil; NMR,δ: 0.96(t,6H,NCH₂CH₃), 2.48(s,3H,C—CH₃),2.96(q,4H, NCH₂CH₃),3.81(s,3H,OCH₃),4.59 (s,2H,SCH₂)Mass(m/e): 382(M⁺), 146 |
| 29-(1) | 3-OCH₃, 2-pyridyl | oil; NMR,δ: 0.88(t,6H,NCH₂CH₃), 2.89(q,4H,NCH₂CH₃),3.79(s,3H, OCH₃),4.47(s,2H,SCH₂)Mass (m/e: 368(M⁺),146 |
| 30-(1) | 2-CH₃, 4-pyridyl | oil |
| 31-(1) | 2-pyridyl | oil; NMR,δ: 0.94(t,6H,NCH₂CH₃), 2.95(q,4H,NCH₂CH₃),4.95(s,2H, SCH₂)Mass(m/e): 339(M⁺+1), 146 |

*note:
NMR is measured in CDCl₃

(2) The products obtained above are treated in the same manner as described in Example 1-(2) to give the compounds shown in Table 4.

TABLE 4

[Structure: (II-b) → pyridine ring A with (CH₂)ₙ-N-C(OS-CH₂-C₆H₄-N(C₂H₅)₂)=N in imidazole ring]

(I-b)

(wherein n = 0)

| Ex. Nos. | Compound(I-b) Ring A | Properties* |
|---|---|---|
| 26-(2) | 4-CH₃, 2-pyridyl | M.p. 110 to 112° C.(recrystallized from ether) |
| 27-(2) | 3-CH₃, 2-pyridyl | M.p. 81 to 83° C.(recrystallized from ether and n-hexane) |
| 28-(2) | 4-OCH₃, 6-CH₃, 2-pyridyl | M.p. 99 to 100° C.(recrystallized from ethyl acetate and n-hexane) |
| 29-(2) | 3-OCH₃, 2-pyridyl | oil; NMR,δ:0.87(t,6H,NCH₂CH₃), 3.81(s,3H,OCH₃), 4.80(ABq,2H,SCH₂) Mass(m/e):384(M⁺),162 |
| 30-(2) | 2-CH₃, 4-pyridyl | M.p. 121 to 123° C.(recrystallized from isopropyl ether) |
| 31-(2) | 2-pyridyl | M.p. 115 to 116° C.(recrystallized from methylene chloride and n-hexane) |

*note:
NMR is measured in CDCl₃

EXAMPLES 32 to 50

(1) The corresponding starting compounds are treated in the same manner as described in Example 1-(1) to give the compounds shown in Table 5.

TABLE 5

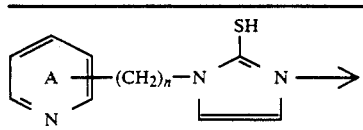
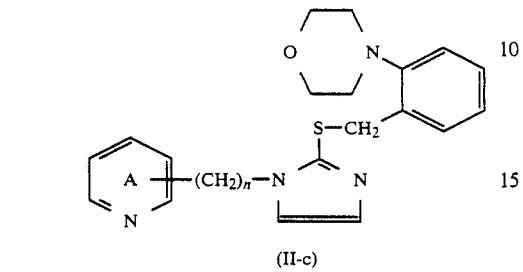

(II-c)
(wherein n = 1 in Example 41, and n = 0 in Examples 32 to 40 and 42 to 50)

| Ex. Nos. | Compound(II-c) Ring A | Properties* |
|---|---|---|
| 32-(1) | 5-Cl, 2-Me pyridyl | M.p. 138.5 to 140° C. (recrystallized from chloroform and n-hexane) |
| 33-(1) | 5-Br, 2-Me pyridyl | M.p. 140 to 150° C. (recrystallized from chloroform and n-hexane) |
| 34-(1) | 5-CF₃, 2-Me pyridyl | M.p. 148 to 151° C. (recrystallized from ethyl acetate and n-hexane) |
| 35-(1) | 3-OCH₃, 6-Me pyridyl | M.p. 119 to 121.5° C. (recrystallized from ethyl acetate and n-hexane) |
| 36-(1) | 3,4-di-OCH₃ pyridyl | oil |
| 37-(1) | 3-OH, 2-Me pyridyl | M.p. 191 to 193° C. (recrystallized from chloroform and n-hexane) |
| 38-(1) | 4-OCH₂CF₃, 2-Me pyridyl | oil; NMR,δ: 2.91(m,4H,NCH₂), 3.80(m,4H,OCH₂), 4.38(q,2H,OCH₂CF₃), 4.57(s,2H,SCH₂) Mass(m/e): 450(M⁺),175 |
| 39-(1) | 4-OCH₃, 2,6-di-Me pyridyl | M.p. 103 to 105° C. (recrystallized from ethyl acetate and n-hexane) |

TABLE 5-continued

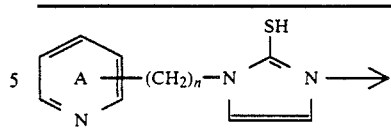
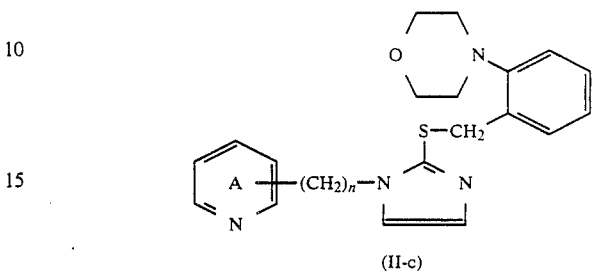

(II-c)
(wherein n = 1 in Example 41, and n = 0 in Examples 32 to 40 and 42 to 50)

| Ex. Nos. | Compound(II-c) Ring A | Properties* |
|---|---|---|
| 40-(1) | 2,4-di-Me pyridyl | oil |
| 41-(1) | 2-pyridyl | oil; NMR,δ: 4.39(s,2H,SCH₂), 5.04(s,2H,NCH₂N) Mass(m/e): 367(M⁺+1),175 |
| 42-(1) | 4-pyridyl | M.p. 137 to 138° C. (recrystallized from ethyl acetate and n-hexane) |
| 43-(1) | 3-CH₃, 2-Me pyridyl | oil; NMR,δ: 2.06(s,3H,CH₃), 4.44(s,2H,SCH₂) Mass(m/e): 366(M⁺),175 |
| 44-(1) | 4-CH₃, 2-Me pyridyl | M.p. 109 to 111° C. (recrystallized from ethyl acetate and n-hexane) |
| 45-(1) | 5-CH₃, 2-Me pyridyl | M.p. 98 to 100° C. (recrystallized from ethyl acetate and isopropyl ether) |
| 46-(1) | 2,6-di-Me pyridyl | M.p. 114 to 116° C. (recrystallized from ethyl acetate and n-hexane) |
| 47-(1) | 2,6-di-Me, 4-CH₃ pyridyl | M.p. 126 to 128° C. (recrystallized from ethyl acetate and n-hexane) |

TABLE 5-continued

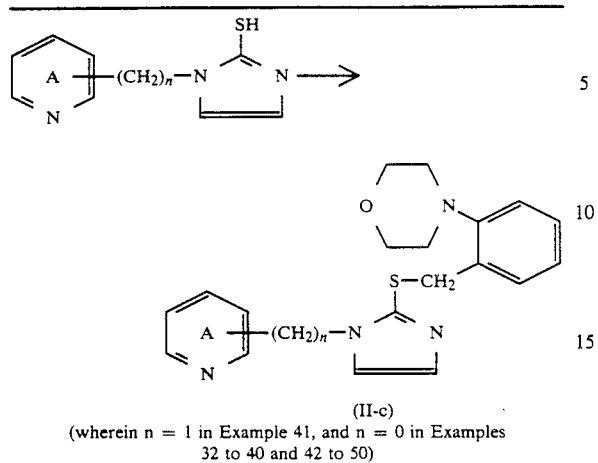

(wherein n = 1 in Example 41, and n = 0 in Examples 32 to 40 and 42 to 50)

| Ex. Nos. | Compound(II-c) Ring A | Properties* |
|---|---|---|
| 48-(1) | (pyridine with OCH3, CH3) | M.p. 124 to 126° C. (recrystallized from ethyl acetate and n-hexane) |
| 49-(1) | (pyridine with NO2, CH3) | M.p. 199 to 202° C. (recrystallized from chloroform and n-hexane) |
| 50-(1) | (pyridine with CH3) | M.p. 112 to 113° C. (recrystallized from ethyl acetate, ether and n-hexane) |

*note:
NMR is measured in CDCl$_3$ (2) The products obtained above are treated in the same manner as described in Example 1-(2) to give the compounds shown in Table 6.

TABLE 6

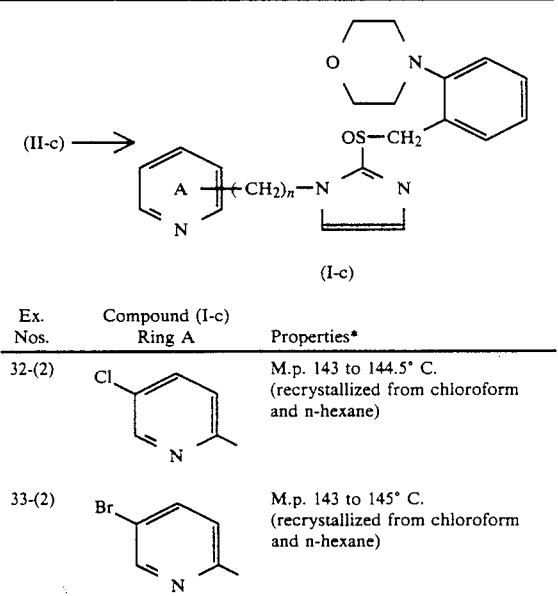

| Ex. Nos. | Compound (I-c) Ring A | Properties* |
|---|---|---|
| 32-(2) | (Cl-pyridine-CH3) | M.p. 143 to 144.5° C. (recrystallized from chloroform and n-hexane) |
| 33-(2) | (Br-pyridine-CH3) | M.p. 143 to 145° C. (recrystallized from chloroform and n-hexane) |

TABLE 6-continued

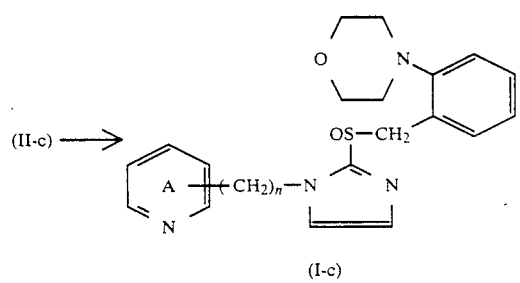

| Ex. Nos. | Compound (I-c) Ring A | Properties* |
|---|---|---|
| 34-(2) | (CF3-pyridine-CH3) | M.p. 143.5 to 144.5° C. (recrystallized from chloroform and n-hexane) |
| 35-(2) | (OCH3-pyridine-CH3) | M.p. 139 to 141° C. (recrystallized from ethyl acetate and n-hexane) |
| 36-(2) | (OCH3, OCH3-pyridine-CH3) | M.p. 178 to 183° C. (recrystallized from chloroform, isopropyl ether and n-hexane) |
| 37-(2) | (OH-pyridine-CH3) | M.p. 161 to 164° C.(decomp. recrystallized from methanol, chloroform and n-hexane) |
| 38-(2) | (OCH2CF3-pyridine-CH3) | M.p. 140 to 144° C. (recrystallized from ethyl acetate and n-hexane) |
| 39-(2) | (OCH3-pyridine with CH3, CH3) | M.p. 151 to 152° C. (recrystallized from ethyl acetate) |
| 40-(2) | (CH3-pyridine) | M.p. 91 to 96° C. (recrystallized from isopropyl ether) |
| 41-(2) | (pyridine) | oil; NMR, $\delta$:4.81 (ABq,2H,SCH$_2$), 5.35(ABq,2H,NCH$_2$N) Mass(m/e):383(M$^+$ + 1),176 |
| 42-(2) | (pyridine) | M.p. 150 to 152° C. (recrystallized from ethyl acetate) |

TABLE 6-continued

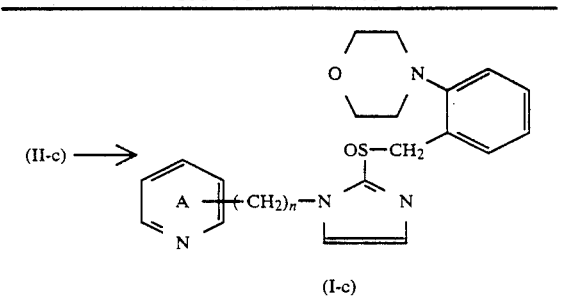

(I-c)

| Ex. Nos. | Compound (I-c) Ring A | Properties* |
|---|---|---|
| 43-(2) | 3-CH₃, 2-methylpyridine | M.p. 129 to 130° C. (recrystallized from ethyl acetate and n-hexane) |
| 44-(2) | 4-CH₃, 2-methylpyridine | M.p. 155.5 to 157.5° C. (recrystallized from chloroform and n-hexane) |
| 45-(2) | 5-CH₃, 2-methylpyridine | M.p. 135 to 137° C. (recrystallized from ethyl acetate) |
| 46-(2) | 3,6-dimethylpyridine | M.p. 124 to 126° C. (recrystallized from ethyl acetate and n-hexane) |
| 47-(2) | 4-CH₃, 2,6-dimethylpyridine | M.p. 133 to 135° C. (recrystallized from ethyl acetate and n-hexane) |
| 48-(2) | 3-OCH₃, 2-methylpyridine | M.p. 130 to 132° C. (recrystallized from ethyl acetate and n-hexane) |
| 49-(2) | 5-NO₂, 2-methylpyridine | M.p. 179.5 to 181.5° C. (recrystallized from chloroform and ethanol) |
| 50-(2) | 2-methylpyridine | M.p. 112 to 115° C. (recrystallized from ethyl acetate) |

(wherein n = 1 in Example 41, and n = 0 in Examples 32 to 40 and 42 to 50)
*note: NMR is measured in CDCl₃

EXAMPLES 51 to 58

(1) The corresponding starting compounds are treated in the same manner as described in Example 1-(1) to give the compounds shown in Table 7.

TABLE 7

Structure showing pyridine-$(CH_2)_n$-N=C(SH)-NH → reacting with piperidinyl-phenyl-$CH_2$-S-containing intermediate to give (II-d)

(II-d)

| Ex. Nos. | Compound (II-d) Ring A | Properties* |
|---|---|---|
| 51-(1) | 4-CH₃, 2-methylpyridine | oil; NMR, δ:1.30–1.90(m,6H, CH₂),2.36(s,3H,C—CH₃), 2.60–3.00(m,4H,NCH₂),4.54(s, 2H, SCH₂)Mass(m/e):364(M⁺), 173 |
| 52-(1) | 5-CH₃, 2-methylpyridine | M.p. 99 to 100° C. (recrystallized from isopropyl ether) |
| 53-(1) | 4-CH₃, 2,6-dimethylpyridine | oil; NMR, δ:1.20–1,84(m,6H, CH₂),2.31(s,3H,CH₃), 2.49(s,3H,CH₃)2.68–2.97(m,4H, NCH₂),4.53(s,2H, SCH₂) Mass(m/e):379(M⁺ + 1),173 |
| 54-(1) | 6-OCH₃, 2-methylpyridine | oil; NMR, δ:1.30–1.85(m,6H, CH₂),2.50–2.95(m,4H,NCH₂), 3.96(s,3H,OCH₃),4.59(s,2H, SCH₂)Mass(m/e):380(M⁺),173 |
| 55-(1) | 3-CH₃, 2-methylpyridine | oil; NMR, δ:1.33–1,73(m,6H, CH₂),2.05(s,3H,C—CH₃), 2.70–2.76(m,4H,NCH₂),4.43(s, 2H, SCH₂)Mass(m/e):364(M⁺), 173 |
| 56-(1) | 3-OCH₃, 2-methylpyridine | M.p. 123.5 to 125.5° C. (recrystallized from ethyl acetate and n-hexane) |
| 57-(1) | 4-OCH₃, 2,6-dimethylpyridine | oil; NMR, δ:1.60(br,6H,CH₂), 2.48(s,3H,C—CH₃),2.77–2.88(m, 4H,NCH₂),3.80(s,3H,OCH₃), 4.55(s,2H, SCH₂)Mass(m/e):394(M⁺),173 |
| 58-(1) | 2-methylpyridine | M.p. 115 to 117° C. (recrystallized from ethyl acetate and n-hexane) |

(wherein n = 0)
*note: NMR is measured in CDCl₃

(2) The products obtained above are treated in the same manner as described in Example 1-(2) to give the compounds shown in Table 8.

TABLE 8

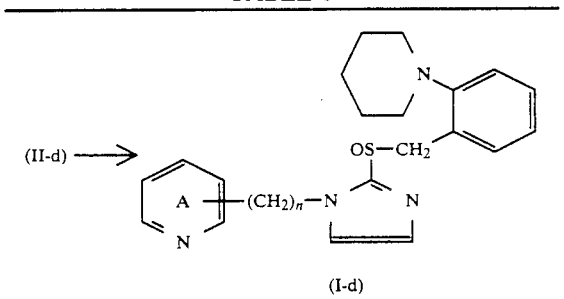

(I-d)

| Ex. Nos. | Compound (I-d) Ring A | Properties* |
|---|---|---|
| 51-(2) | 4-CH$_3$ pyridine (2-yl) | M.p. 62 to 64° C. (recrystallized from chloroform and isopropyl ether) |
| 52-(2) | 5-CH$_3$ pyridine (2-yl) | M.p. 108 to 111° C. (recrystallized from isopropyl alcohol and isopropyl ether) |
| 53-(2) | 4,6-(CH$_3$)$_2$ pyridine (2-yl) | M.p. 143 to 145° C. (recrystallized from ethyl acetate) |
| 54-(2) | 6-OCH$_3$ pyridine (2-yl) | M.p. 152 to 153° C. (recrystallized from ethyl acetate) |
| 55-(2) | 3-CH$_3$ pyridine (2-yl) | M.p. 94 to 96° C. (recrystallized from ethyl acetate and n-hexane) |
| 56-(2) | 3-OCH$_3$ pyridine (2-yl) | oil; NMR,δ:1.4–1.8(m,6H, CH$_2$),2.5–2.9(m,4H,NCH$_2$), 3.80(s,3H,OCH$_3$),4.75(ABq,2H, SCH$_2$)FABMass(m/e): 397(M$^+$ + 1),174 |
| 57-(2) | 4-OCH$_3$-6-CH$_3$ pyridine (2-yl) | M.p. 129–131° C. (recrystallized from ethyl acetate) |
| 58-(2) | pyridine (2-yl) | M.p. 94 to 96° C. (recrystallized from ethyl acetate and n-hexane) |

(wherein n = 0)
*note: NMR is measured in CDCl$_3$

EXAMPLES 59 to 64

(1) The corresponding starting compounds are treated in the same manner as described in Example 1-(1) to give the compounds shown in Table 9.

TABLE 9

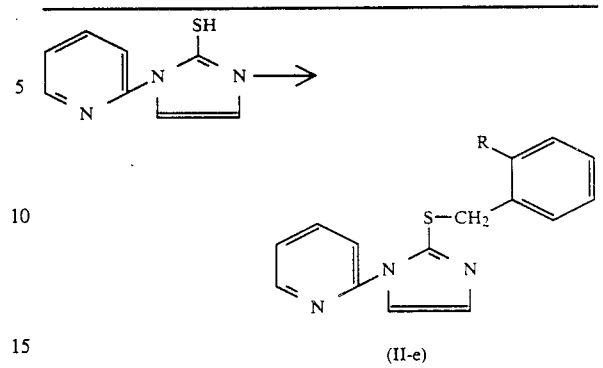

(II-e)

| Ex. Nos. | Compound (II-e) R | Properties* |
|---|---|---|
| 59-(1) | —N(n-C$_3$H$_7$)$_2$ | oil; NMR, δ:0.79(t,6H,J=7Hz, CCH$_3$),4.61(s,2H, SCH$_2$) Mass (m/e) :367(M$^+$ + 1), 190) |
| 60-(1) | —CH$_2$N(CH$_3$)$_2$ | M.p. 48 to 52° C. (recrystallized from ethyl acetate and n-hexane) |
| 61-(1) | —NH—cyclohexyl | oil; NMR, δ:1.0–2.1(m,10H,CH$_2$), 3.1–3.5(br,1H,CHN), 4.44(s,2H, SCH$_2$),4.7–5.0(br,1H,NH) Mass(m/e):364(M$^+$),188 |
| 62-(1) | N-methylimidazol-2-yl | oil; NMR, δ:4.23(s,2H, SCH$_2$) Mass(m/e):333(M$^+$) |
| 63-(1) | —H | M.p. 69 to 71° C. (recrystallized from isopropyl ether and n-hexane) |
| 64-(1) | —OCH$_3$ | M.p. 68 to 70° C. (recrystallized from ether and isopropyl ether) |

*note: NMR is measured in CDCl$_3$ (2) The products obtained above are treated in the same manner as described in Example 1-(2) to give the compounds shown in Table 10.

TABLE 10

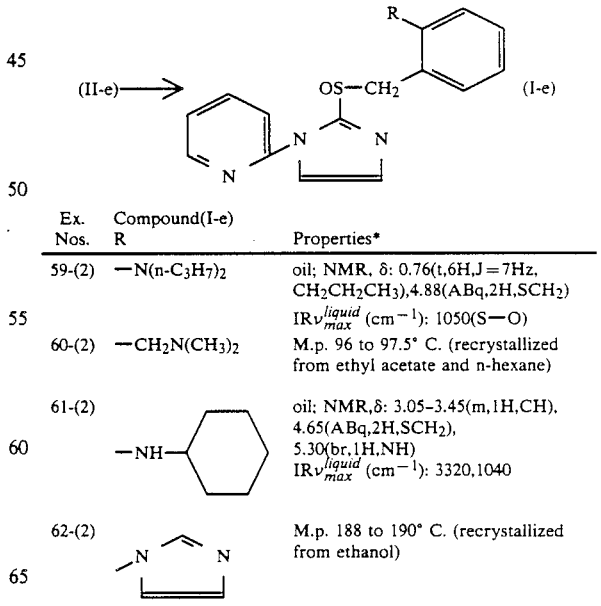

(I-e)

| Ex. Nos. | Compound(I-e) R | Properties* |
|---|---|---|
| 59-(2) | —N(n-C$_3$H$_7$)$_2$ | oil; NMR, δ: 0.76(t,6H,J=7Hz, CH$_2$CH$_2$CH$_3$),4.88(ABq,2H,SCH$_2$) IRν$_{max}^{liquid}$ (cm$^{-1}$): 1050(S—O) |
| 60-(2) | —CH$_2$N(CH$_3$)$_2$ | M.p. 96 to 97.5° C. (recrystallized from ethyl acetate and n-hexane) |
| 61-(2) | —NH—cyclohexyl | oil; NMR,δ: 3.05–3.45(m,1H,CH), 4.65(ABq,2H,SCH$_2$), 5.30(br,1H,NH) IRν$_{max}^{liquid}$ (cm$^{-1}$): 3320,1040 |
| 62-(2) | N-methylimidazol-2-yl | M.p. 188 to 190° C. (recrystallized from ethanol) |
| 63-(2) | —H | M.p. 151 to 153° C. (recrystallized from ethanol and ether) |

TABLE 10-continued

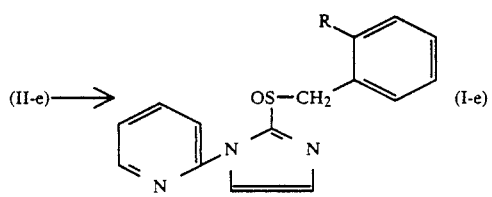

| Ex. Nos. | Compound(I-e) R | Properties* |
|---|---|---|
| 64-(2) | —OCH₃ | M.p. 148 to 151° C. (recrystallized from ethanol) |

*note: NMR is measured in CDCl₃

EXAMPLES 65 to 66

(1) The corresponding starting compounds are treated in the same manner as described in Example 1-(3) to give the compounds shown in Table 11.

TABLE 11

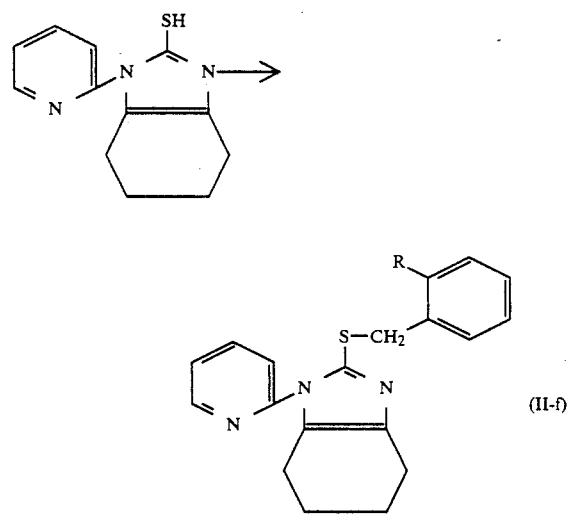

| Ex. Nos. | Compound(II-f) R | Properties* |
|---|---|---|
| 65-(1) | —N(CH₃)₂ | oil; NMR, δ: 1.70–1.97(m,4H,CH₂), 2.40–2.87(m,4H,=CCH₂), 2.60(s,6H,N(CH₃)₂), 4.39(s,2H,SCH₂) Mass(m/e): 364(M⁺), 134 |
| 66-(1) | —N⟨  ⟩O (morpholino) | oil; NMR, δ: 1.76–1.89(m,4H,CH₂), 2.43–2.71(m,4H,=CCH₂), 2.73–2.87(m,4H,N(CH₂), 3.68–3.81(m,4H,OCH₂), 4.40(S,2H,SCH₂) Mass(m/e): 406(M⁺) |

*note: NMR is measured in CDCl₃

(2) The products obtained above are treated in the same manner as described in Example 1-(2) to give the compounds shown in Table 12.

TABLE 12

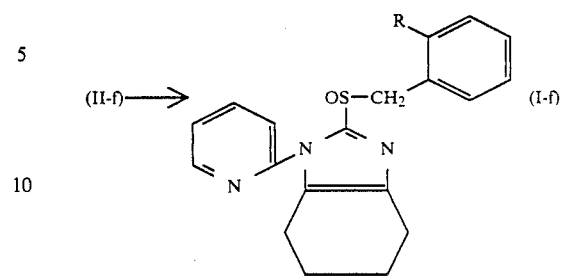

| Ex. Nos. | Compound(I-f) R | Properties* |
|---|---|---|
| 65-(2) | —N(CH₃)₂ | oil; NMR, δ: 2.59(s,6H,N(CH₃)₂), 4.80(ABq,2H,SCH₂) FABMass(m/e): 381(M⁺ + 1) |
| 66-(2) | —N⟨  ⟩O (morpholino) | oil; NMR,δ: 4.82(ABq,2H,SCH₂) FABMass(m/e): 423(M⁺ + 1) |

*note: NMR is measured in CDCl₃

EXAMPLE 67

(1) A solution of 7.53 g of 2-(2-dimethylaminobenzylthio)-1,3a,4,5,5,6a-hexahydro-6a-hydroxy-1-(2-pyridyl)-cyclopenta[d]imidazole and a catalytic amount of p-toluenesulfonic acid in 100 ml of toluene is refluxed for 1 hour. The reaction mixture is evaporated to remove the solvent, water is added to the residue, and the aqueous mixture is neutralized with an aqueous sodium bicarbonate solution. The mixture is extracted with chloroform. The extract is dried and evaporated to remove the solvent, whereby 3.94 g of 1,4,5,6-tetrahydro-2-(2-dimethylaminobenzylthio)-1-(2-pyridyl)cyclopenta[d]imidazole are obtained.

Yield 55%.

M.p. 115° to 117° C. (recrystallized from ethyl acetate and n-hexane).

(2) The product obtained above is treated in the same manner as described in Example 1-(2) to give 1,4,5,6-tetrahydro-2-(2-dimethylaminobenzylsulfinyl)-1-(2-pyridyl)cyclopenta[d]imidazole.

Yield 74%.

M.p. 139.5° to 141° C. (recrystallized from ethyl acetate and n-hexane).

EXAMPLES 68 to 70

(1) The corresponding starting compounds are treated in the same manner as described in Example 67-(1) to give the compounds shown in Table 13.

TABLE 13

| Ex. Nos. | Compound(II-g) R | Properties |
|---|---|---|
| 68-(1) | —N(C$_2$H$_5$)$_2$ | M.p. 106 to 108° C. (recrystallized from ethyl acetate and n-hexane) |
| 69-(1) | 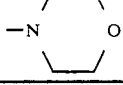 | M.p. 120 to 122.5° C. (recrystallized from ethyl acetate and n-hexane) |
| 70-(1) |  | M.p. 115 to 116° C. (recrystallized from isopropyl ether) |

(2) The products obtained above are treated in the same manner as described in Example 1-(2) to give the compounds shown in Table 14.

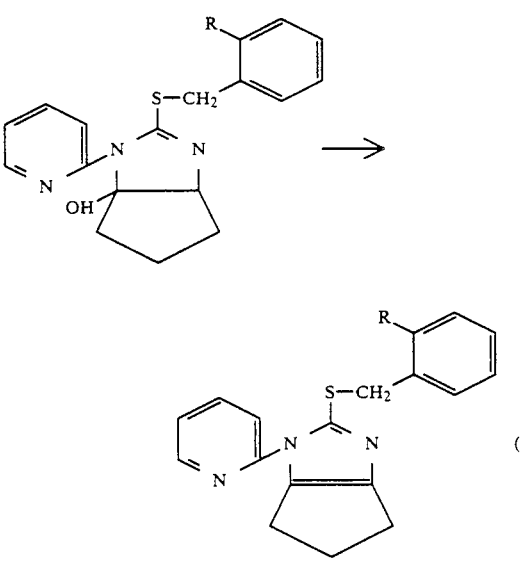

| Ex. Nos. | Compound(I-g) R | Properties |
|---|---|---|
| 68-(2) | —N(C$_2$H$_5$)$_2$ | M.p. 107 to 109° C. (recrystallized from ethyl acetate and n-hexane) |
| 69-(2) | 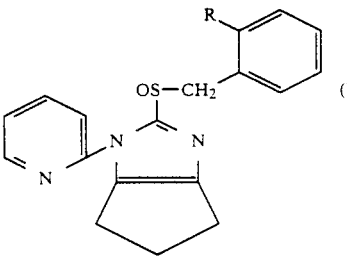 | M.p. 147 to 148.5° C. (recrystallized from ethyl acetate and n-hexane) |

-continued

| Ex. Nos. | Compound(I-g) R | Properties |
|---|---|---|
| 70-(2) | —N O | M.p. 135 to 136.5° C. (recrystallized from ethyl acetate) |

EXAMPLE 71

(1) 1-(2-pyridyl)-2-mercaptoimidazole and (2,4,6-trimethylphenyl)sulfonylaminobenzyl chloride are treated in the same manner as described in Example 1-(1) to give 1-(2-pyridyl)-2-[2-(2,4,6-trimethylpenyl)-sulfonylaminobenzylthio]imidazole.

Yield 87%.

M.p. 152° to 156° C. (recrystallized from isopropyl alcohol).

(2) A mixture of 2 g of the product obtained above, 2.5 ml of anisole and 15 ml of methanesulfonic acid is stirred at room temperature for 20 hours. After the reaction, the mixture is added to water and extracted with ethyl acetate. The extract is washed with a saturated aqueous sodium chloride solution, dried and evaporated to remove the solvent, whereby 1.1 g of 1-(2-pyridyl)-2-(2-aminobenzylthio)imidazole are obtained as an oil.

Yield 93%.

Mass(m/e):282(M+), 106.

$^1$H-NMR(CDCl$_3$,δ):3.9(br,2H,NH$_2$),4.43(s,2H, SCH$_2$).

(3) The product obtained above is treated in the same manner as described in Example 1-(2) to give 1-(2-pyridyl)-2-(2-aminobenzylsulfinyl)imidazole.

M.p. 145° to 146° C. (recrystallized from isopropyl alcohol).

EXAMPLE 72

(1) A mixture of 4.8 g of 1-(2-pyridyl)-2-(2-aminobenzylthio)imidazole, 5 ml of acetic acid anhydride and 50 ml of pyridine is stirred at room temperature for 16 hours. The solvent is distilled off, and the residue is crystallized with toluene and collected by filtration, whereby 4.31 g of 1-(2-pyridyl)-2-(2-acetylaminobenzylthio)imidazole are obtained.

Yield 78%.

M.p. 150° to 151° C. (recrystallized from isopropyl alcohol).

(2) The product obtained above is treated in the same manner as described in Example 1-(2) to give 1-(2-pyridyl)-2-(2-acetylaminobenzylsulfinyl)imidazole.

M.p. 172° to 173° C. (recrystallized from isopropyl alcohol).

EXAMPLE 73

(1) 100 mg of 60% sodium hydride are suspended in 2 ml of dimethyl formamide, and a solution of one g of 1-(2-pyridyl)-2-[2-(2,4,6-trimethylphenyl)sulfonylaminobenzylthio]imidazole in 2 ml of dimethyl formamide is added thereto under ice-cooling. The mixture is stirred at room temperature for 30 minutes, and 320 mg of methyl iodide are added thereto. The mixture is stirred for 2 hours. The reaction mixture is poured into water, and the resultant oily product is extracted with ethyl acetate. The extract is dried and evaporated. The residue is purified by silica gel column chromatography (solvent; n-hexane:ethyl acetate=3:2), whereby 0.76 g of 1-(2-pyridyl)-2-{2-[N-methyl-N-(2,4,6-trimethylphenyl)sulfonylamino]benzylthio}imidazole is obtained.

M.p. 131° to 133° C. ( recrystallized from ethyl acetate).

(2) The product obtained above is treated in the same manner as described in Example 71-(2) to give 1-(2-pyridyl)-2-(2-methylaminobenzylthio)imidazole as an oil.

Yield 92%.

Mass (m/e):2.96(M+), 120.

$^1$H-NMR(CDCl$_3$,δ):2.83(d,3H,J=3 Hz,NCH$_3$), 4.42(s,2H,SCH$_2$), 5.20(br,1H,NH).

(3) The product obtained above is treated in the same manner as described in Example 1-(2) to give 1-(2-pyridyl)-2-(2-methylaminobenzylsulfinyl)imidazole.

M.p. 135° to 137° C. (recrystallized from ethyl acetate).

EXAMPLE 74

(1) 1-(2-pyridyl)-2-(2-acetylaminobenzylthio)imidazole is treated in the same manner as described in Example 73-(1) to give 1-(2-pyridyl)-2-[2-(N-methyl-N-acetylamino)benzylthio]imidazole as an oil.

Yield 78%.

Mass(m/e):338(M+), 120.

$^1$M-NMR(CDCl$_3$,δ): 1.76(s,3H, COCH$_3$, 3.20(s,3H,NCH$_3$), 4.39(s,2H,SCH$_2$).

(2) The product obtained above is treated in the same manner as described in Example 1-(2) to give 1-(2-pyridyl)-2-[2-(N-methyl-N-acetylamino)benzylsulfinyl]imidazole.

M.p. 188° to 189° C. (recrystallized from chloroform and isopropyl ethyl).

EXAMPLE 75

(1) 2-(2-phthalimidobenzylthio)-1,3a,4,5,6,6a-hexahydro-6a-hydroxy-1-(2-pyridyl)cyclopenta[d]imidazole is treated in the same manner as described in Example 67-(1) to give 1,4,5,6-tetrahydro-1-(2-pyridyl)-2-(phthalimidobenzylthio)cyclopenta[d]imidazole.

M.p. 196° to 197° C. (recrystallized from chloroform and ethyl acetate).

(2) A mixture of 1.80 g of the product obtained above, 0.22 g of hydrazine hydrate and 100 ml of methanol is refluxed for 5 hours. After the reaction mixture is cooled, the solvent is distilled off, and methylene chloride is added to the residue. Insoluble materials are filtered off. The filtrate is washed with water, dried and evaporated to remove the solvent. The crystalline residue is recrystallized from a mixture of ethyl acetate and n-hexane, whereby 1.06 g of 1,4,5,6-tetrahydro-1-(2-pyridyl)-2-(aminobenzylthio)cyclopenta[d]imidazole are obtained as pale yellow plates.

Yield 83%.

M.p. 121° to 123° C.

(3) A solution of 0.27 g of acetyl chloride in 5 ml of methylene chloride is added dropwise to 20 ml of methylene chloride containing 1.0 g of the product obtained above and 0.35 g of triethylamine. Said dropwise addition is carried out under ice-cooling. After 1 hour, the reaction mixture is washed with a saturated aqueous sodium bicarbonate solution and water, dried and evaporated to remove the solvent. The crystalline residue is recrystallized from a mixture of chloroform and ethyl acetate, whereby 0.83 g of 1,4,5,6-tetrahydro-1-(2-pyridyl)-2-(acetylaminobenzylthio)cyclopenta[d]imidazole is obtained.

Yield 74%.

M.p. 214 to 217 (decomp.).

(4) The product obtained above is treated in the same manner as described in Example 1-(2) to give 1,4,5,6-tetrahydro-1-(2-pyridyl)-2-(acetylaminobenzylsulfinyl)cyclopenta[d]imidazole.

M.p. 188° to 191° C. (decomp., recrystallized from ethyl acetate and n-hexane).

EXAMPLE 76

(1) 1-(4-pyridyl)-2-mercaptoimidazole and 2-phthalimidobenzyl chloride are treated in the same manner as described in Example 1-(1) to give 1-(4-pyridyl)-2-(2-phthalimidobenzylthio)imidazole.

M.p. 145° to 147° C. (recrystallized from ethanol).

(2) The product obtained above is treated in the same manner as described in Example 75-(2) to give 1-(4-pyridyl)-2-(2-aminobenzylthio)imidazole as an oil.

Mass(m/e): 282(M+), 106.

$^1$H-NMR(CDCl$_3$,δ): 4.21 (br,2H,NH$_2$),4.30(s,2H,SCH$_2$).

(3) The product obtained above is treated in the same manner as described in Example 75-(3) to give 1-(4-pyridyl)-2-(2-acetylaminobenzylthio)imidazole.

M.p. 153° to 155° C. (recrystallized from ethyl acetate and n-hexane).

(4) The product obtained above is treated in the same manner as described in Example 1-(2) to give 1-(4-pyridyl)-2-(2-acetylaminobenzylsulfinyl)imidazole.

M.p. 147° to 149° C. (recrystallized from isopropyl alcohol and isopropyl ether).

EXAMPLE 77

(1) 1-(2-pyridylmethyl)-2-mercaptoimidazole and 2-phthalimidobenzyl chloride are treated in the same manner as described in Example 1-(1) to give 1-(2-pyridylmethyl)-2-(2-phthalimidobenzylthio)imidazole.

M.p. 80° to 83° C. (recrystallized from ethanol).

2) The product obtained above is treated in the same manner as described in Example 75-(2) to give 1-(2-pyridylmethyl)-2-(2-aminobenzylthio)imidazole as an oil.

Mass (m/e): 296(M+), 106.

$^1$H-NMR(CDCl$_3$,δ): 4.21(s,2H,SCH$_2$),4.31 (br,2H,NH$_2$), 5.10(s,2H,NCH$_2$).

(3) The product obtained above is treated in the same manner as described in Example 1-(2) to give 1-(2-pyridylmethyl)-2-(2-aminobenzylsulfinyl)imidazole.

Mass (m/e): 312(M+), 106.

$^1$H-NMR(CDCl$_3$,δ): 4.26(br,2H,NH$_2$),4.59(ABq,2H, NCH$_2$), 5.29(ABq,2H,NCH$_2$).

EXAMPLE 78

(1) A solution containing n-butyl lithium (15%) in 14.3 ml of a n-hexane are added at −60° C. to 50 ml of tetrahydrofuran containing 4.33 g of o-(N-methyl-N-phenylamino)benzylalcohol. After 20 minutes, 2.67 g of triethylamine are added to the mixture, and a solution of 5.03 g of p-toluenesulfonyl chloride in 20 ml of tetrahydrofuran is added dropwise thereto. The mixture is stirred at −20° C. for 1 hour. 5.0 g of triethylamine and 3.59 g of 1-(2-pyridyl)-2-mercaptoimidazole are further added thereto. After 2 hours, ethyl acetate is added to the reaction mixture. Then, the mixture is washed with water, dried and evaporated to remove the solvent. The residue is purified by column chromatography (solvent; ethyl acetate:chloroform=1:9), whereby 4.55 g of 1-(2-pyridyl)-2-(N-methyl-N-phenhylaminobenzylthio)imidazole are obtained.

Yield 60%.

M.p. 90° to 92° C. (recrystallized from ethyl acetate and m-hexane).

(2) The product obtained above is treated in the same manner as described in Example 1-(2) to give 1-(2-pyridyl)-2-(N-methyl-N-phenylaminobenzylsulfinyl-)imidazole.

M.p. 137° to 139° C. (recrystallized from isopropyl alcohol and n-hexane).

EXAMPLES 79 to 84

(1) The corresponding starting compounds are tested in the same manner as described in Example 78-(1) to give the compounds shown in Table 15.

TABLE 15

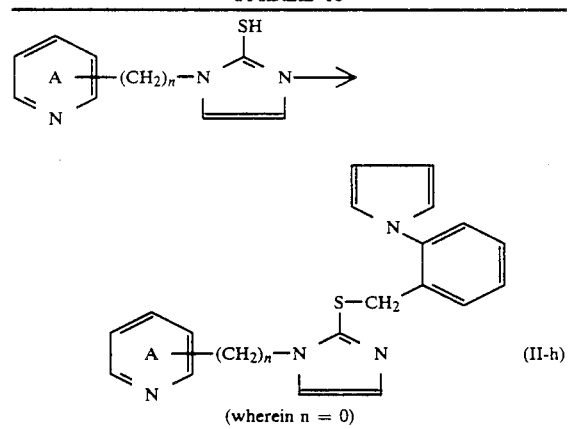

(wherein n = 0)

| Ex. Nos. | Compound(II-h) Ring A | Properties* |
|---|---|---|
| 79-(1) | (OCH3, N) | oil; NMR,δ: 3.96(s,3H,OCH3), 4.33(s,2H,SCH2),6.27(t,2H,=CH—) Mass(m/e): 362(M+) |
| 80-(1) | (CH3, N) | oil; NMR,δ: 2.38(s,3H,C—CH3), 4.26(s,2H,SCH2),6.25(t,2H,=CH—) 6.81(t,2H,N=CH—) Mass(m/e): 349(M+),192 |
| 81-(1) | (CH3, N) | oil; NMR,δ: 2.03(s,3H,C—CH3), 4.11(s,2H,SCH2),6.23(t,2H,=CH—) 6.71(t,2H,N=CH—) Mass(m/e): 346(M+),192 |

TABLE 15-continued

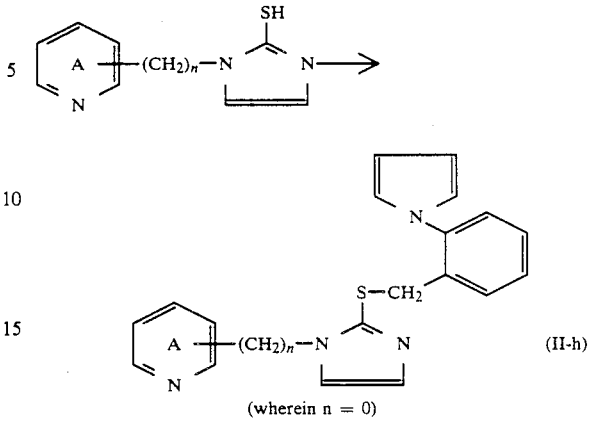

(wherein n = 0)

| Ex. Nos. | Compound(II-h) Ring A | Properties* |
|---|---|---|
| 82-(1) | (OCH3, N) | oil; NMR,δ: 3.79(s,3H,OCH3), 4.38(s,2H,SCH2),6.24(t,2H,=CH—) 6.72(t,2H,N=CH—) Mass(m/e): 362(M+),208 |
| 83-(1) | (OCH3, CH3, N) | oil |
| 84-(1) | (N) | M.p. 93 to 95° C. (recrystallized from ethyl acetate and n-hexane) NMR,δ: 4.52(s,2H,SCH2), 6.30 and 6.83(t,2H,J=2Hz, H—H, H—H) —N Mass(m/e): 332(M+),156 |

*note: NMR is measured in CDCl3

(2) The products obtained above are treated in the same manner as described in Example 1-(2) to give the compounds shown in Table 16.

TABLE 16

(II-h) ⟶

| Ex. Nos. | Compound(I-h) Ring A | Properties* |
|---|---|---|
| 79-(2) | (OCH3, N) | M.p. 112 to 114° C. (recrystallized from ethyl acetate and n-hexane) |

TABLE 16-continued

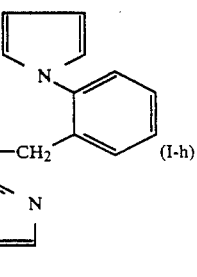

(II-h) → (I-h)  (wherein n = 0)

| Ex. Nos. | Compound(I-h) Ring A | Properties* |
|---|---|---|
| 80-(2) | CH₃ (4-methylpyridyl) | M.p. 106 to 120° C. (recrystallized from chloroform and n-hexane) |
| 81-(2) | CH₃ (3-methylpyridyl) | M.p. 113 to 115° C. (recrystallized from ethyl acetate and n-hexane) |
| 82-(2) | OCH₃ (3-methoxypyridyl) | oil; NMR,δ: 3.84(s,3H,OCH₃), 4.56(s,2H,SCH₂),6.24 and 6.76(t,2H, H—H / H—H, —N) Mass(m/e): 379(M⁺),156 |
| 83-(2) | OCH₃, CH₃ (disubstituted pyridyl) | M.p. 127 to 128.5° C. (recrystallized from ethyl acetate and n-hexane) |
| 84-(2) | (pyridyl) | M.p. 116 to 118° C. (recrystallized from ethyl acetate and n-hexane) |

*note: NMR is measured in CDCl₃

EXAMPLE 85

(1) 19.6 g of 1-(5-nitro-2-pyridyl)-2-[2-(dimethylamino)benzylthio]imidazole are dissolved in 400 ml of the mixture of conc. hydrochloric acid and a 70% aqueous ethanol (1:5). A solution of 82.7 g of tin (II) chloride dihydrate in 100 ml of water is added dropwise thereto at 80° C., and the mixture is stirred for 1 hour at the same temperature. The reaction mixture is made alkaline with an aqueous sodium hydroxide solution, and insoluble materials are filtered off. The filtrate is extracted with ethyl acetate, dried and evaporated to remove the solvent. The residue is purified by silica gel column chromatography (solvent; chloroform:methanol=30:1), and crystallized with ether. The crystals are collected by filtration, whereby 6.27 g of 1-(5-amino-2-pyridyl)-2-[2-(dimethylamino)benzylthio]imidazole are obtained. M.p. 134° to 138° C.

(2) The product obtained is treated in the same manner as described in Example 1-(2) to give 1-(5-amino-2-pyridyl)-2-[2-(dimethylamino)benzylsulfinyl]imidazole.

M.p. 140° to 143° C. (recrystallized from ethanol and ether).

EXAMPLE 86

(1) 1-(5-nitro-2-pyridyl)-2-mercaptoimidazole and 2-morpholinobenzyl chloride are treated in the same manner as described in Example 1-(1) to give 1-(5-nitro-2-pyridyl)-2-(2-morpholinobenzylthio)imidazole.

M.p. 100° to 202° C. (recrystallized from chloroform and n-hexane).

(2) 7.95 g of the product obtained above are dissolved in 120 ml of acetic acid, and subjected to catalytic hydrogenation in the presence of 2.5 g of 10% palladium-carbon at room temperature under atmospheric pressure. After the reaction, the catalyst is filtered off, and the filtrate is evaporated to remove the solvent. Water is added to the residue, and the aqueous mixture is neutralized with a saturated aqueous sodium bicarbonate solution. The crystalline precipitates are collected by filtration, and recrystallized from chloroform and n-hexane, whereby 5.92 g of 1-(5-amino-2-pyridyl)-2-(2-morpholinobenzylthio)imidazole are obtained.

Yield 81%.

M.p. 178° to 181° C.

(3) The product obtained above is treated in the same manner as described in Example 1-(2) to give 1-(5-amino-2-pyridyl)-2-(2-morpholinobenzylsulfinyl)imidazole.

M.p. 190° to 192° C. (decomp. recrystallized from chloroform and n-hexane).

EXAMPLE 87

(1) 1-(5-amino-2-pyridyl)-2-(2-morpholinobenzylthio)imidazole is treated in the same manner as described in Example 75-(3) to give 1-(5-acetylamino-2-pyridyl)-2-(2-morpholinobenzylthio)imidazole.

Yield 78%.

M.p. 164° to 167° C. (recrystallized from chloroform and n-hexane).

(2) The product obtained above is treated in the same manner as described in Example 1-(2) to give 1-(5-acetylamino-2-pyridyl)-2-(2-morpholinobenzylsulfinyl)imidazole.

M.p. 207° to 209° C. (decomp. recrystallized from chloroform and n-hexane).

EXAMPLES 88 to 91

(1) The corresponding starting compounds are treated in the same manner as described in Example 1-(1) to give the compounds shown in Table 17.

TABLE 17

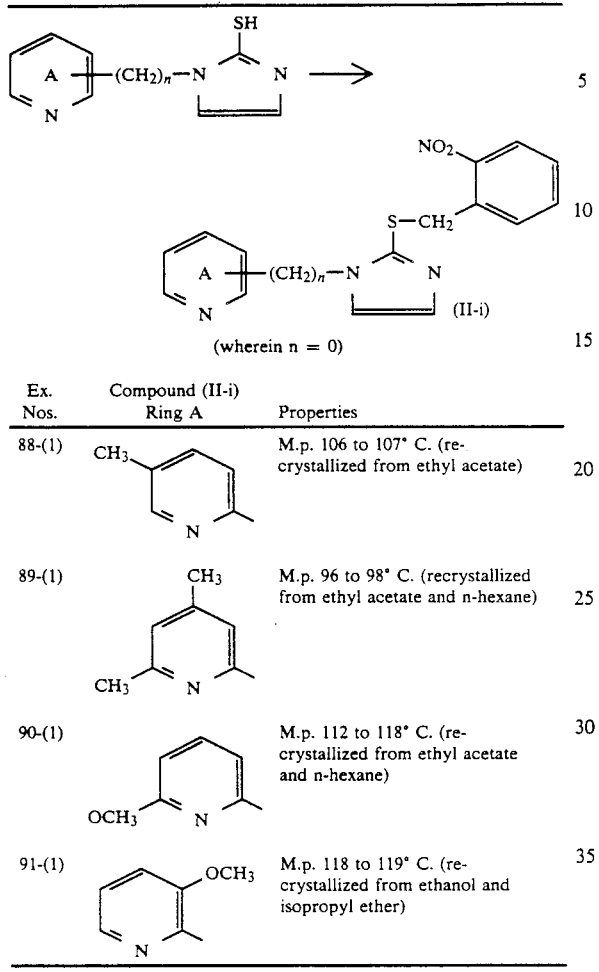

(wherein n = 0)

| Ex. Nos. | Compound (II-i) Ring A | Properties |
|---|---|---|
| 88-(1) | CH₃ (pyridine) | M.p. 106 to 107° C. (recrystallized from ethyl acetate) |
| 89-(1) | CH₃, CH₃ (pyridine) | M.p. 96 to 98° C. (recrystallized from ethyl acetate and n-hexane) |
| 90-(1) | OCH₃ (pyridine) | M.p. 112 to 118° C. (recrystallized from ethyl acetate and n-hexane) |
| 91-(1) | OCH₃ (pyridine) | M.p. 118 to 119° C. (recrystallized from ethanol and isopropyl ether) |

(2) The products obtained above are treated in the same manner as described in Example 86-(2) to give the compounds shown in Table 18.

TABLE 18

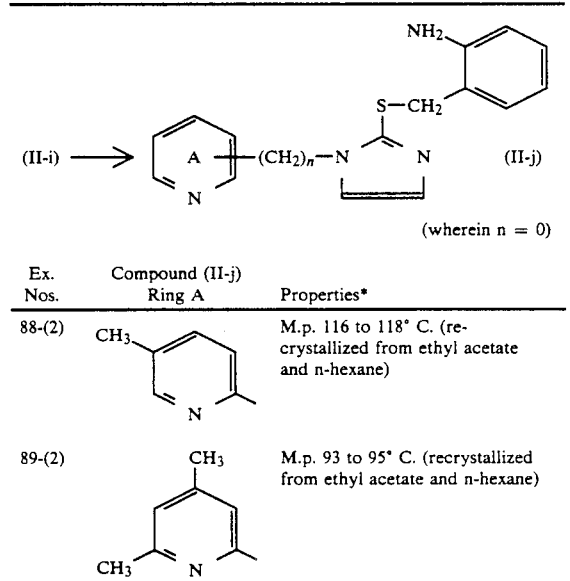

(wherein n = 0)

| Ex. Nos. | Compound (II-j) Ring A | Properties* |
|---|---|---|
| 88-(2) | CH₃ (pyridine) | M.p. 116 to 118° C. (recrystallized from ethyl acetate and n-hexane) |
| 89-(2) | CH₃, CH₃ (pyridine) | M.p. 93 to 95° C. (recrystallized from ethyl acetate and n-hexane) |

TABLE 18-continued

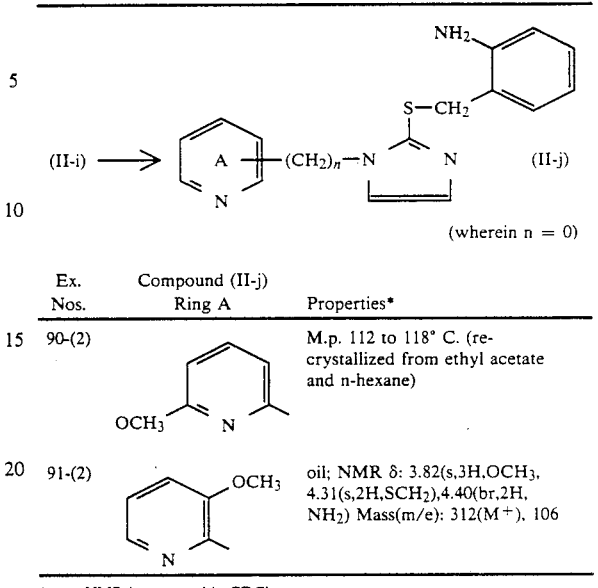

(wherein n = 0)

| Ex. Nos. | Compound (II-j) Ring A | Properties* |
|---|---|---|
| 90-(2) | OCH₃ (pyridine) | M.p. 112 to 118° C. (recrystallized from ethyl acetate and n-hexane) |
| 91-(2) | OCH₃ (pyridine) | oil; NMR δ: 3.82(s,3H,OCH₃, 4.31(s,2H,SCH₂),4.40(br,2H, NH₂) Mass(m/e): 312(M⁺), 106 |

*note: NMR is measured in CDCl₃

(3) The products obtained above are treated in the same manner as described in Example 75-(3) to give the compounds shown in Table 19.

TABLE 19

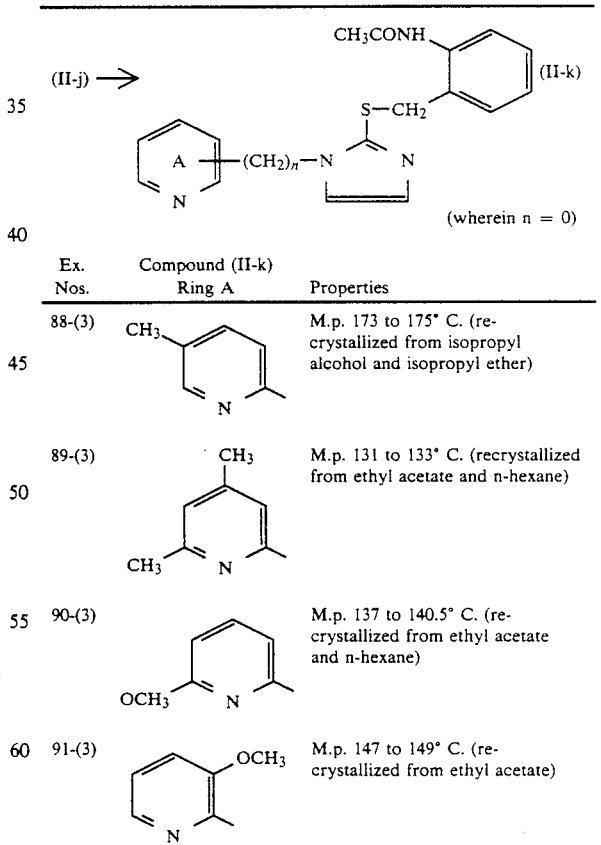

(wherein n = 0)

| Ex. Nos. | Compound (II-k) Ring A | Properties |
|---|---|---|
| 88-(3) | CH₃ (pyridine) | M.p. 173 to 175° C. (recrystallized from isopropyl alcohol and isopropyl ether) |
| 89-(3) | CH₃, CH₃ (pyridine) | M.p. 131 to 133° C. (recrystallized from ethyl acetate and n-hexane) |
| 90-(3) | OCH₃ (pyridine) | M.p. 137 to 140.5° C. (recrystallized from ethyl acetate and n-hexane) |
| 91-(3) | OCH₃ (pyridine) | M.p. 147 to 149° C. (recrystallized from ethyl acetate) |

(4) The products obtained above are treated in the same manner as described in Example 1-(2) to give the compounds shown in Table 20.

TABLE 20

(II-k) → [structure with CH₃CONH, OS—CH₂, A—(CH₂)ₙ—N, imidazole] (I-i)

(wherein n = 0)

| Ex. Nos. | Compound (I-i) Ring A | Properties |
|---|---|---|
| 88-(4) | CH₃-pyridyl (3-methylpyridin-2-yl) | M.p. 192 to 194° C. (recrystallized from methylene chloride and n-hexane) |
| 89-(4) | 4,6-dimethylpyridin-2-yl | M.p. 185 to 193° C. (recrystallized from methylene chloride and n-hexane) |
| 90-(4) | 6-methoxypyridin-2-yl (OCH₃) | M.p. 155.5 to 157.5° C. (recrystallized from methylene chloride and n-hexane) |
| 91-(4) | 3-methoxypyridin-2-yl (OCH₃) | M.p. 110 to 113° C. (recrystallized from ethyl acetate) |

EXAMPLE 92

(1) 1-(2-pyridylmethyl)-2-(2-aminobenzylthio)imidazole is treated in the same manner as described in Example 75-(3) to give 1-(2-pyridylmethyl)-2-(2-acetylaminobenzylthio)imidazole.

Mass (m/e): 338(M+), 106.

¹H-NMR(CDCl₃,δ): 2.29(s,3H,COCH₃), 4.31(s,2H,SCH₂),5.10(s,2H,NCH₂).

(2) The product obtained above is treated in the same manner as described in Example 1-(2) to give 1-(2-pyridylmethyl)-2-(2-acetylaminobenzylsulfinyl)imidazole.

M.p. 146° to 148° C. (recrystallized from ethyl acetate and n-hexane).

EXAMPLE 93

(1) 0.26 ml of acetyl chloride is added to a mixture of 0.98 g of 1-(5-amino-2-pyridyl)-2-[2-(dimethylamino)benzylthio]imidazole, 1 ml of triethylamine and 30 ml of methylene chloride under ice-cooling. The mixture is stirred at the same temperature for 2 hours, washed with water and a saturated aqueous sodium bicarbonate solution, dried and evaporated to remove the solvent. The residue is purified by silica gel column chromatography (solvent; chloroform:methanol=30:1), and crystallized with isopropyl ether. The crystals are collected by filtration, whereby 0.82 g of 1-(5-acetylamino-2-pyridyl)-2-[2-(dimethylamino)benzylthio]imidazole is obtained.

M.p. 137° to 139° C.

(2) The product obtained above is treated in the same manner as described in Example 1-(2) to give 1-(5-acetylamino-2-pyridyl)-2-[2-(dimethylamino)benzylsulfinyl]imidazole.

M.p. 168° to 170° C. (recrystallized from ethanol and ether).

EXAMPLE 94

(1) 1.4 g of acetic acid anhydride are added to 2.5 ml of formic acid, and the mixture is stirred at 60° C. for 30 minutes. The reaction solution is cooled in an ice bath, a solution of 1.07 g of 1-(4,6-dimethyl-2-pyridyl)-2-(2-aminobenzylthio)imidazole in 4 ml of formic acid is added thereto, and the mixture is stirred at room temperature for 1 hour. After the reaction, the solvent is distilled off. Water is added to the residue, and the aqueous mixture is made alkaline with potassium carbonate. The mixture is then extracted with ethyl acetate, dried and evaporated to remove the solvent. The residue is purified by silica gel column chromatography (solvent; ethyl acetate:n-hexane=1:1). The crude crystals obtained above are recrystallized from a mixture of ethyl acetate and n-hexane, whereby 0.64 g of 1-(4,6-dimethyl-2-pyridyl)-2-(2-formylaminobenzylthio)imidazole is obtained.

Yield 55%.

M.p. 124° to 126.5° C.

(2) The product obtained above is treated in the same manner as described in Example 1-(2) to give 1-(4,6-dimethyl-2-pyridyl)-2-(2-formylaminobenzylsulfinyl)imidazole.

M.p. 160° to 162° C. (decomp. recrystallized from methylene chloride and n-hexane).

EXAMPLE 95

(1) A solution of 1.7 g of potassium carbonate in 10 ml of water is added to 10 ml of methylene chloride containing 1.2 g of 1-(2-pyridyl)-2-(2-aminobenzylthio)imidazole. 0.65 g of benzoyl chloride is added thereto under vigourous stirring, the mixture is stirred at room temperature for 1 hour. After the reaction, the organic layer is separated therefrom, washed with water, dried and evaporated to remove the solvent. The crude crystals obtained above are recrystallized from a mixture of isopropyl alcohol and isopropyl ether, whereby 1.55 g of 1-(2-pyridyl)-2-(2-benzoylaminobenzylthio)imidazole are obtained.

Yield 95%.

M.p. 132° to 133° C.

(2) The product obtained above is treated in the same manner as described in Example 1-(2) to give 1-(2-pyridyl)-2-(2-benzoylaminobenzylsulfinyl)imidazole.

M.p. 109° to 111° C. (recrystallized from ethyl acetate).

EXAMPLES 96 to 97

(1) The corresponding starting compounds are treated in the same manner as described in Example 95-(1) to give the compounds shown in Table 21.

TABLE 21

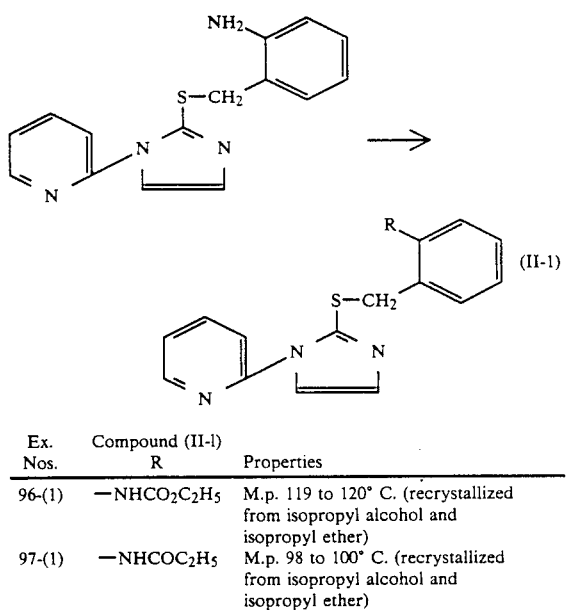

| Ex. Nos. | Compound (II-1) R | Properties |
|---|---|---|
| 96-(1) | —NHCO₂C₂H₅ | M.p. 119 to 120° C. (recrystallized from isopropyl alcohol and isopropyl ether) |
| 97-(1) | —NHCOC₂H₅ | M.p. 98 to 100° C. (recrystallized from isopropyl alcohol and isopropyl ether) |

(2) The products obtained above are treated in the same manner as described in Example 1-(2) to give the compounds shown in Table 22.

TABLE 22

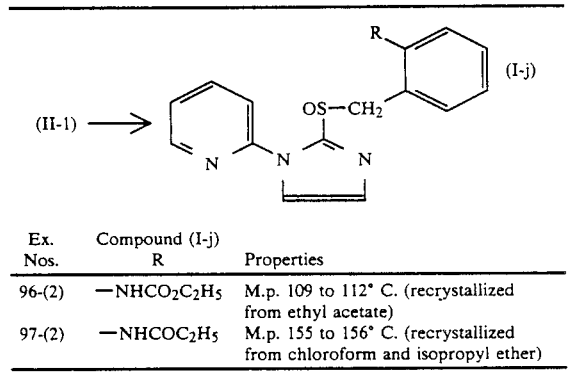

| Ex. Nos. | Compound (I-j) R | Properties |
|---|---|---|
| 96-(2) | —NHCO₂C₂H₅ | M.p. 109 to 112° C. (recrystallized from ethyl acetate) |
| 97-(2) | —NHCOC₂H₅ | M.p. 155 to 156° C. (recrystallized from chloroform and isopropyl ether) |

EXAMPLE 98

(1) 0.96 ml of acetyl chloride is added dropwise to 100 ml of methylene chloride containing 2.94 g of 1-(3-hydroxy-2-pyridyl)-2-(2-dimethylaminobenzylthio)imidazole and 3.76 ml of triethylamine. Said dropwise addition is carried out in under ice-cooling. After 2 hour, the reaction mixture is washed with water, dried and evaporated to remove the solvent. The residue is purified by silica gel column chromatography (solvent; chloroform:acetone=30:1), and recrystallized from a mixture of ethyl acetate and n-hexane, whereby 2.03 g of 1-(3-acetoxy-2-pyridyl)-2-(2-dimethylaminobenzylthio)imidazole are obtained as colorless needles.

Yield 63%.

M.p. 85° to 87° C.

(2) The product obtained above is treated in the same manner as described in Example 1-(2) to give 1-(3-acetoxy-2-pyridyl)-2-(2-dimethylaminobenzylsulfinyl)imidazole is obtained as an oil.

FABMass(m/e): 385(M⁺+1), 134.

¹H-NMR(CDCl₃,δ): 2.19(s,3H,COCH₃),2.57(s,6H,N(CH₃)₂), 4.77(ABq,2H,SCH₂).

IR $\nu_{max}^{Nujol}$ (cm⁻¹): 1770 (NHCO), 1045 (S—O).

EXAMPLE 99

(1) 1-(3-hydroxy-2-pyridyl)-2-(2-morpholinobenzylthio)imidazole is treated in the same manner as described in Example 98-(1) to give 1-(3-acetoxy-2-pyridyl)-2-(2-morpholinobenzylthio)imidazole.

Yield 73%.

M.p. 89° to 91° C. (recrystallized from ethyl acetate and n-hexane).

(2) The product obtained above is treated in the same manner as described in Example 1-(2) to give 1-(3-acetoxy-2-pyridyl)-2-(2-morpholinobenzylsulfinyl)imidazole.

M.p. 104° to 107° C. (recrystallized from ethyl acetate and n-hexane).

EXAMPLE 100

(1) 0.48 g of methanesulfonyl chloride is added to 10 ml of methylene chloride containing 10.9 g of 1-(4,6-dimethyl-2-pyridyl)-2-(2-aminobenzylthio)imidazole and 0.5 ml of triethylamine. Said dropwise addition is carried out under ice-cooling. After 1 hour, the reaction mixture is washed with water, dried and evaporated to remove the solvent. The residue is purified by silica gel column chromatography (solvent; chloroform:ethyl acetate=10:1), and recrystallized from a mixture of ethyl acetate and n-hexane, whereby 1.0 g of 1-(4,6-dimethyl-2-pyridyl)-2-(2-methanesulfonylaminobenzylthio)imidazole as colorless needles.

Yield 73%.

M.p. 121° to 123° C.

(2) The product obtained above is treated in the same manner as described in Example 1-(2) to give 1-(4,6-dimethyl-2-pyridyl)-2-(2-methanesulfonylaminobenzylsulfinyl)imidazole.

138° to 142° C. (recrystallized from methylene chloride and n-hexane).

EXAMPLE 101

(1) 3.26 g of 1-(3-hydroxy-2-pyridyl)-2-(2-dimethylaminobenzylthio)imidazole are dissolved in 100 ml of dimethyl formamide, and 0.48 g of 60% sodium hydride is added thereto. After the mixture is stirred for 20 minutes, 1.3 ml of isopropyl bromide are added dropwise thereto, and the mixture is further stirred at room temperature for 17 hours. The reaction mixture is poured into ice water, extracted with ethyl acetate, dried and evaporated to remove the solvent. The residue is recrystallized from a mixture of ethyl acetate and n-hexane, whereby 2.47 g of 1-(3-isopropoxy-2-pyridyl)-2-(2-dimethylaminobenzylthio)imidazole are obtained.

Yield 67%.

M.p. 85° to 87° C.

(2) The product obtained above is treated in the same manner as described in Example 1-(2) to give 1-(3-isopropoxy-2-pyridyl)-2-(2-dimethylaminobenzylsulfinyl)imidazole.

Mass (m/e): 384 (M⁺), 134.

¹H-NMR (CDCl₃, δ): 1.32 and 1.34 (d, 3H, CH₃, respectively), 2.63 (s, 6H, N(CH₃)₂), 4.81 (ABq, 2H, SCH₂).

EXAMPLES 102 TO 103

(1) The corresponding starting compounds are treated in the same manner as described in Example 101-(1) to give the compounds shown in Table 23.

TABLE 23

(II-o)

[Structure: Ring A with (CH₂)ₙ—N connected to imidazole with S—CH₂ linked to phenyl bearing morpholino group]

(wherein n = 0)

| Ex. Nos. | Compound (II-o) Ring A | Properties |
|---|---|---|
| 102-(1) | [pyridine with O-i-C₃H₇ and methyl] | M.p. 117 to 119° C. (recrystallized from ethyl acetate and n-hexane) |
| 103-(1) | [pyridine with OCH₂CH=CH₂ and methyl] | M.p. 87 to 89° C. (recrystallized from ethyl acetate and n-hexane) |

(2) The products obtained above are treated in the same manner as described in Example 1-(2) to give the compounds shown in Table 24.

TABLE 24

(II-o) → (I-k)

[Structure: Ring A with (CH₂)ₙ—N connected to imidazole with OS—CH₂ linked to phenyl bearing morpholino group]

(wherein n = 0)

| Ex. Nos. | Compound (I-k) Ring A | Properties* |
|---|---|---|
| 102-(2) | [pyridine with O-i-C₃H₇ and methyl] | M.p. 120 to 122° C. (recrystallized from ethyl acetate and n-hexane) |
| 103-(2) | [pyridine with OCH₂CH=CH₂ and methyl] | oil; NMR, δ: 2.7–3.0(m,4H, OC$\underline{H}_2$), 3.6–3.9(m,4H, NC$\underline{H}_2$), 4.58(dt,2H, OC$\underline{H}_2$CH=), 4.81(ABq,2H, SC$\underline{H}_2$), 5.97(m,1H,CH=), 5.1–5.5(m,2H,CH₂=) FABMass(m/e): 425(M⁺ + 1),176 |

*note: NMR is measured in CDCl₃

EXAMPLE 104

3.42 g of 80% m-chloroperbenzoic acid are added to 100 ml of chloroform containing 1.5 g of 1-(4-pyridyl)-2-(2-dimethylaminobenzylthio)imidazole. Said addition is carried out under ice-cooling. After the mixture is stirred for 1 hour, 8.36 g of sodium hydrosulfite are added thereto, and allowed to stand at room temperature, for 2 hours. The reaction mixture is washed with a saturated aqueous sodium bicarbonate solution and water, dried and evaporated to remove the solvent. The residue is purified by silica gel column chromatography (solvent; chloroform: methanol=40:1), and recrystallized from a mixture of chloroform and isopropyl ether, whereby 0.91 g of 1-(4-pyridyl)-2-(2-dimethylaminobenzylsulfonyl)imidazole is obtained.

M.p. 132° to 135° C.

PREPARATION OF STARTING COMPOUNDS

Preparation 1

(1) A solution of 3.76 g of 2-aminopyridine and 7 g of 2,2-diethoxyethyl isothiocyanate in toluene is refluxed. After the reaction, the solvent is distilled off, and the residue is recrystallized from a mixture of ethyl acetate and n-hexane, whereby 9 g of N-(2,2-diethoxyethyl)-N'-(2-pyridyl)thiourea are obtained.

M.p. 126° to 128° C.

(2) A solution of 8.94 g of the product obtained above and a small amount of conc. hydrochloric acid in acetic acid is refluxed. After the reaction, the solution is evaporated to remove the solvent. The residue is dissolved in water, and sodium bicarbonate is added thereto. The crystalline precipitates are collected by filtration, whereby 4.91 g of 1-(2-pyridyl)-2-mercaptoimidazole are obtained.

M.p. 159° to 161° C. (recrystallized from isopropyl alcohol, isopropyl ether and n-hexane).

Preparations 2 to 25

The corresponding starting compounds are treated in the same manner as described in Preparation 1-(1) and (2) to give the compounds shown in Table 25.

TABLE 25

[Scheme: A—(CH₂)ₙ—NH₂ (VI) + Z=C=NCH₂CH(OR³)₂ (VII) → Ring A—(CH₂)ₙ—N connected to imidazole bearing SH, R¹, R² (III)]

(wherein n = 1 in Pr. No. 2, n = 0 in Pr. Nos. 3 to 24, and n = 2 in Pr. No. 25, R¹ and R² are hydrogen atom, R³ is ethyl, and Z is sulfur atom)

| Pr. Nos. | Compound (III) Ring A | Properties |
|---|---|---|
| 2 | [pyridine with methyl] | M.p. 181 to 183° C. (recrystallized from ethanol) |
| 3 | [pyridine with CH₃ and methyl] | M.p. 209.5 to 211.5° C. (recrystallized from methanol) |

TABLE 25-continued

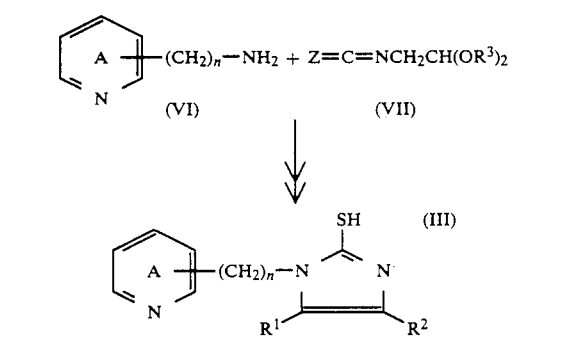

(wherein n = 1 in Pr. No. 2, n = 0 in Pr. Nos. 3 to 24, and n = 2 in Pr. No. 25, $R^1$ and $R^2$ are hydrogen atom, $R^3$ is ethyl, and Z is sulfur atom)

| Pr. Nos. | Compound (III) Ring A | Properties |
|---|---|---|
| 4 | 5-NO₂, 2-pyridyl | M.p. 267 to 269° C. (recrystallized from ethanol) |
| 5 | 2,4-diCH₃, 6-pyridyl | M.p. 170 to 172° C. (recrystallized from methanol) |
| 6 | 3-OCH₃, 2-pyridyl | M.p. 223 to 225° C. (recrystallized from ethanol) |
| 7 | 3-CH₃, 2-pyridyl | M.p. 187 to 190° C. (recrystallized from ethanol) |
| 8 | 5-Br, 2-pyridyl | M.p. 227 to 229° C. (recrystallized from ethanol) |
| 9 | 6-OCH₃, 2-pyridyl | M.p. 188 to 190° C. (recrystallized from ethanol) |
| 10 | 4-CH₃, 2-pyridyl | M.p. 166 to 168° C. (recrystallized from ethanol) |
| 11 | 5-Cl, 2-pyridyl | M.p. 222 to 225° C. (recrystallized from ethanol) |
| 12 | 5-CF₃, 2-pyridyl | M.p. 205° C. (decomp. recrystallized from ethyl acetate and isopropyl ether) |

TABLE 25-continued

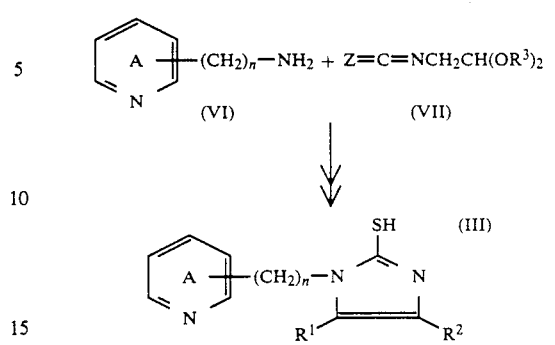

(wherein n = 1 in Pr. No. 2, n = 0 in Pr. Nos. 3 to 24, and n = 2 in Pr. No. 25, $R^1$ and $R^2$ are hydrogen atom, $R^3$ is ethyl, and Z is sulfur atom)

| Pr. Nos. | Compound (III) Ring A | Properties |
|---|---|---|
| 13 | 3,4-diOCH₃, 2-pyridyl | M.p. 205 to 207° C. (recrystallized from ethanol, isopropyl ether and n-hexane) |
| 14 | 4-OCH₃, 6-CH₃, 2-pyridyl | M.p. 163 to 166° C. (recrystallized from ethyl acetate and n-hexane) |
| 15 | 4-OCH₂CF₃, 2-pyridyl | M.p. 162 to 165° C. (recrystallized from ethyl acetate and n-hexane) |
| 16 | 3-OH, 2-pyridyl | M.p. 181 to 183° C. (recrystallized from methanol) |
| 17 | 2-CH₃, 4-pyridyl | M.p. 208 to 211° C. (recrystallized from ethyl acetate) |
| 18 | 4-pyridyl | M.p. 263 to 265° C. (recrystallized from ethanol) |
| 19 | 3-pyridyl | M.p. 251 to 253° C. (recrystallized from methanol) |
| 20 | 4-OCH₃, 2-pyridyl | M.p. 157 to 159° C. (recrystallized from methanol) |

TABLE 25-continued

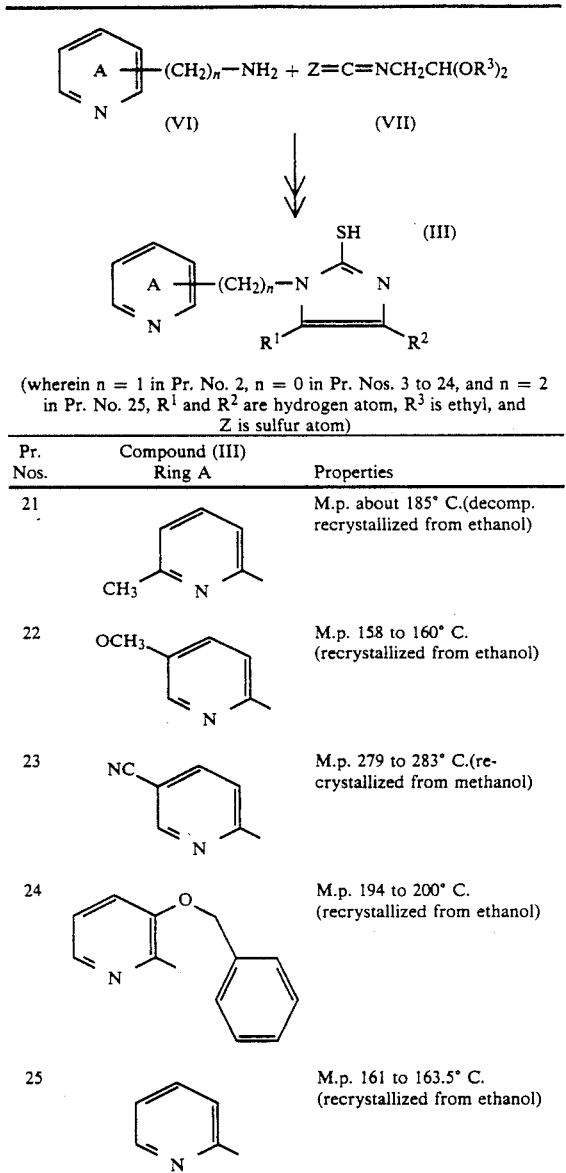

(wherein n = 1 in Pr. No. 2, n = 0 in Pr. Nos. 3 to 24, and n = 2 in Pr. No. 25, R¹ and R² are hydrogen atom, R³ is ethyl, and Z is sulfur atom)

| Pr. Nos. | Compound (III) Ring A | Properties |
|---|---|---|
| 21 | (3,6-dimethylpyridin-2-yl, CH₃ at 6, CH₃ at 3) | M.p. about 185° C.(decomp. recrystallized from ethanol) |
| 22 | (5-methoxy-pyridin-2-yl, OCH₃) | M.p. 158 to 160° C. (recrystallized from ethanol) |
| 23 | (5-cyano-pyridin-2-yl, NC) | M.p. 279 to 283° C.(recrystallized from methanol) |
| 24 | (3-benzyloxy-pyridin-2-yl) | M.p. 194 to 200° C. (recrystallized from ethanol) |
| 25 | (pyridin-2-yl) | M.p. 161 to 163.5° C. (recrystallized from ethanol) |

Preparation 26

(1) A solution of 57.96 g of o-dimethylcarbamoylbenzoic acid in tetrahydrofuran is added dropwise to a tetrahydrofuran suspension of 34.05 g of sodium borohydride. After the reaction at room temperature, 170.3 g of boron trifluoride etherate are added dropwise thereto, and the mixture is further refluxed. After cooling, a solution of 54 g of oxalic acid in water and methanol is added thereto, and the mixture is further refluxed. The reaction mixture is condensed and extracted with ethyl acetate under an alkaline condition. The extract is evaporated to remove the solvent, and the residue is distilled under reduced pressure, whereby 19.04 g of o-dimethylaminomethylbenzyl alcohol are obtained.

B.p. 106° to 109° C. (4 mmHg).

(2) 2.89 g of thionyl chloride are added dropwise to a methylene chloride solution of 2.9 g of the product obtained above. After the reaction at room temperature, the mixture is diluted with ether. The crystalline precipitates are collected by filtration, whereby 3.78 g of o-dimethylaminomethylbenzylchloride hydrochloride are obtained.

M.p. 143° to 147° C.

Preparation 27

(1) To a tetrahydrofuran solution of 5.12 g of N-phenylanthranilic acid, 32.2 ml of a hexane solution of n-bytyl lithium and a solution of 4.42 g of methyl iodide in tetrahydrofuran are added successively at −60° C. and the mixture is reacted at room temperature. After the reaction, water is added thereto, and the aqueous mixture is extracted with ethyl acetate under an acidic condition. The extract is evaporated to remove the solvent, whereby 5.06 g of N-methyl-N-phenyl anthranilic acid are obtained as an oil.

Yield 93%.

Mass (m/e): 227 (M+).

$^1$H-NMR (CDCl$_3$, δ): 3.22 (s, 3H, NCH$_3$).

IR $\nu_{max}^{liquid}$ (cm$^{-1}$): 1690 (COOH).

(2) A solution of 5.06 g of N-methyl-N-phenyl anthranilic acid in tetrahydrofuran is added dropwise to a tetrahydrofuran suspension of 1.7 g of lithium aluminum hydride under ice-cooling. After the reaction at room temperature, the mixture is cooled in an ice bath. Water and a saturated aqueous sodium sulfate solution are added to the mixture, and insoluble materials are filtered off. The filtrate is evaporated to remove the solvent, and the residue is purified by silica gel column chromatography, whereby 4.33 g of o-N-methyl-N-phenylaminobenzyl alcohol are obtained as a colorless oil.

Mass (m/e): 213 (M+).

$^1$H-NMR (CDCl$_3$, δ): 2.10 (t, 1h, J=6 Hz, OH), 3.21 (s, 3H, NCH$_3$), 4.56 (d, 2H, J=6 Hz, CH$_2$O).

IR $\nu_{max}^{liquid}$ (cm$^{-1}$): 3360.

Preparation 28

A solution of 9 g of ethyl o-(1-pyrrolyl)benzoate in ether is added dropwise to an ether suspension of 2.4 g of lithium aluminum hydride under ice-cooling. After the reaction, water and a saturated aqueous sodium sulfate solution are added to the mixture, and insoluble materials are filtered off. The filtrate is evaporated to remove the solvent, and the residue is distilled under reduced pressure, whereby 6.3 g of o-(1-pyrrolyl)benzyl alcohol are obtained.

B.p. 120° to 135° C. (3 to 4 mmHg).

Mass (m/c): 173 (M+).

$^1$H-NMR (CDCl$_3$, δ): 4.52 (s, 2H, CH$_2$O), 6.30 and 6.83 (respectively, t, 2H, J=2 Hz,

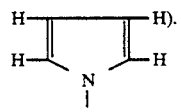

H).

IR $\nu_{max}^{liquid}$ (cm$^{-1}$): 3380.

Preparation 29

A mixture of 6.82 g of 2-aminocyclohexanone hydrochloride, 6.21 g of 2-pyridylisothiocyanate dimer and 100 ml of toluene is stirred under heating. When the temperature is cooled down to 50° C., 4.61 g of triethylamine are added dropwise thereto. After the reaction, water is added to the reaction mixture, and the aqueous mixture is extracted with ethyl acetate. The extract is washed with a saturated sodium chloride solution, dried and evaporated to remove the solvent, whereby 8.2 g of N-(2-pyridyl)-N'-(2-oxocyclohexyl)thiourea are obtained.

Yield 72%.

M.p. 149° to 151° C.

Preparation 30

2-aminocyclopentanone hydrochloride is treated in the same manner as described in Preparation 29 to give 2-mercapto-1,3a,4,5,6,6a-hexahydro-6a-hydroxy-1-(2-pyridyl)cyclopenta[d]imidazole.

Yield 55%.

M.p. 126° to 127° C.

Preparation 31

N-(2-pyridyl)-N'-(2-oxocyclohexyl)thiourea is treated in the same manner as described in Example 67-(1) to give 1-(2-pyridyl)-4,5,6,7-tetrahydrobenzimidazol-2-thione.

M.p. 203° to 204° C. (recrystallized from ethyl acetate and n-hexane).

Preparations 32 to 36

2-mercapto-1,3a,4,5,6,6a-hexahydro-6a-hydroxy-1-(2-pyridyl)cyclopenta[d]imidazole and the corresponding starting compounds are treated in the same manner as described in Example 1-(1) to give the compounds shown in Table 26.

TABLE 26

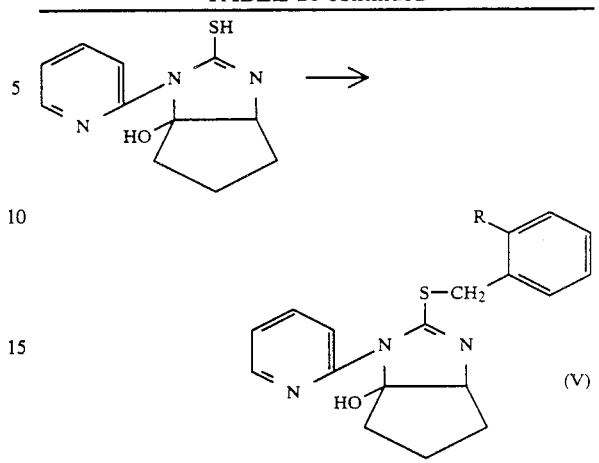

| Pr. Nos. | compound (V) R | Properties |
|---|---|---|
| 32 | —N(CH₃)₂ | oil |
| 33 | —N(C₂H₅)₂ | oil |
| 34 | —N⟨pyrrolidinyl⟩ | oil |
| 35 | —N⟨morpholinyl⟩ | oil |

TABLE 26-continued

| Pr. Nos. | compound (V) R | Properties |
|---|---|---|
| 36 | phthalimido | M.p. 155.5 to 158° C. (recrystallized from ethyl acetate) |

Preparation 37

(1) 24.2 g of ethyl o-fluorobenzoate and 9.8 g of imidazole are heated in the presence of sodium hydride, whereby 23 g of ethyl o-imidazolylbenzoate are obtained.

B.p. 165° to 167° C. (2 mmHg).

(2) 5 g of the product obtained above are treated in the same manner as described in Preparation 28 to give 3.4 g of o-imidazolylbenzyl alcohol.

(3) 3.4 g of the product obtained above are treated in the same manner as described in Preparation 26-(2) to give 3.3 g of o-imiazolylbenzyl chloride are obtained.

M.p. 160° to 161° C. (recrystallized from ethanol and ether).

What is claimed is:

1. An imidazole derivative of the formula:

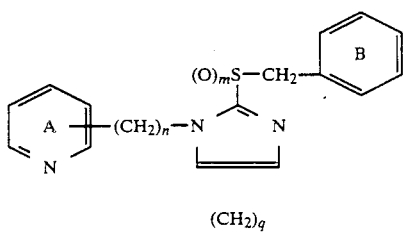

wherein Ring A is a 2-, 3- or 4-pyridyl group which may be unsubstituted or substituted by one or two substituent(s) selected from the group consisting of halogen atom, lower alkyl group, lower alkoxy group, phenyl-lower alkoxy group, nitro group, amino group, lower alkanoylamino group, N-lower alkyl-N-lower alkanoylamino group, mono- or di(lower alkyl) amino group, lower alkanoyloxy group, cyano group, trihalogeno-lower alkyl group, trihalogeno-lower alkoxy group, lower alkenyloxy group and hydroxy group; Ring B is a phenyl group being substituted on the 2- or 3-position by imidazolyl group, morpholino group, pyrrolyl group, phthalimido group, or piperidino group; m is 0, 1 or 2; n is 0, 1 or 2; and q is 3 or 4, or a pharmaceutically acceptable acid addition salt thereof.

2. The compound claimed in claim 1, in which m is 1 or 2.

3. The compound claimed in claim 2, in which Ring A is 2- or 4-pyridyl group having one or two substituent(s) selected from a $C_{1-4}$ alkyl group, a $C_{1-4}$ alkoxy group and a $C_{7-8}$ phenylalkoxy group; Ring B is a phenyl group having one substituent on the 2- or 3-position selected from the group consisting of morpholino group, 1-pyrrolyl group and piperidino group; and m is 1.

4. The compound claimed in claim 2, in which Ring A is a 2-pyridyl group; m is 1; and n is 0.

5. The compound claimed in claim 3, in which Ring A is 2- or 4- pyridyl group, a 3-, 4- or 5-($C_{1-4}$ alkoxy)-2-pyridyl group, a 3-, 4-, 5- or 6-($C_{1-4}$ alkyl)-2-pyridyl group, a 3-($C_{7-8}$ phenylalkoxy)-2-pyridyl group, a 2-($C_{1-4}$ alkyl)-4-pyridyl group or a 4-($C_{1-4}$ alkoxy)-6-($C_{1-4}$ alkyl)-2-pyridyl group; and Ring B is 2-morpholinophenyl group, 2-(1-pyrrolyl)phenyl group, or 2-piperidinophenyl group.

6. The compound claimed in claim 5, in which Ring A is 2- or 4-pyridyl group, 3-, 4- or 5-methoxy-2-pyridyl group, 3-, 4-, 5- or 6-methyl-2-pyridyl group, 3-benzyloxy-2-pyridyl group, 2-methyl-4-pyridyl group or 4-methoxy-6-methyl-2-pyridyl group; and Ring B is 2-morpholinophenyl group 2-(1-pyrrolyl)phenyl group or 2-piperidinophenyl group.

7. The compound claimed in claim 3, in which Ring A is 2-pyridyl group or a 2-pyridyl group having one substituent selected from a $C_{1-4}$ alkyl group; Ring B is a phenyl group which is mono substituted on the 2-position with morpholino group, pyrrolyl group or piperidine group; and n is 0.

8. The compound claimed in claim 7 in which Ring A is 2-pyridyl group or a 3-($C_{1-4}$ alkyl)-2-pyridyl group; and Ring B is 2-morpholinophenyl group, 2-(1-pyrrolyl)phenyl group or 2-piperidinophenyl group.

9. The compound claimed in claim 8, in which Ring A is a 2-pyridyl group or a 3-methyl-2-pyridyl group; and Ring B is 2-morpholinophenyl group, 2-(1-pyrrolyl)phenyl group or 2-piperidinophenyl group.

10. The compound according to claim 1 wherein m=0.

11. The compound according to claim 4, which is 1,4,5,6-tetrahydro-1-(2-pyridyl)-2-[2-(morpholino)benzylsulfinyl]cyclopenta[d]imidazole or a pharmaceutically acceptable acid addition salt thereof.

12. A pharmaceutical composition for the treatment of ulcers which comprises an antiulcer effective amount of the compound claimed in claim 2 and a pharmaceutically acceptable carrier therefor.

13. A pharmaceutical composition for the treatment of ulcers which comprises an antiulcer effective amount of the compound claimed in claim 5 and a pharmaceutically acceptable carrier therefor.

14. A pharmaceutical composition for the treatment of ulcers which comprises an antiulcer effective amount of the compound claimed in claim 8 and a pharmaceutically acceptable carrier therefor.

15. A pharmaceutical composition for the treatment of ulcers which comprises an antiulcer effective amount of the compound claimed in claim 4 and a pharmaceutically acceptable carrier therefor.

16. A pharmaceutical composition for the treatment of ulcers which comprises an antiulcer effective amount of the compound claimed in claim 11 and a pharmaceutically acceptable carrier therefor.

17. A method for treatment or prophylaxis of a peptic ulcer diseases in a warm-blooded animal which comprises administering to said warm-blooded animal a pharmaceutically effective amount of the compound claimed in claim 2.

18. A method for treatment or prophylaxis of a peptic ulcer diseases in a warm-blooded animal which comprises administering to said warm-blooded animal a pharmaceutically effective amount of the compound claimed in claim 5.

19. A method for treatment or prophylaxis of a peptic ulcer diseases in a warm-blooded animal which comprises administering to said warm-blooded animal a pharmaceutically effective amount of the compound claimed in claim 8.

20. A method for treatment of prophylaxis of a peptic ulcer diseases in a warm-blooded animal which comprises administering to said warm-blooded animal a pharmaceutically effective amount of the compound claimed in claim 4.

21. A method for treatment or prophylaxis of a peptic ulcer diseases in a warm-blooded animal which comprises administering to said warm-blooded animal a pharmaceutically effective amount of the compound claimed in claim 11.

* * * * *

UNITED STATES PATENT AND TRADEMARK OFFICE
CERTIFICATE OF CORRECTION

PATENT NO. : 5,002,945
DATED : March 26, 1991
INVENTOR(S) : HONMA et al.

It is certified that error appears in the above-identified patent and that said Letters Patent is hereby corrected as shown below:

Column 52, lines 50-58   Delete the formula under Claim No. 1 and insert the following formula:

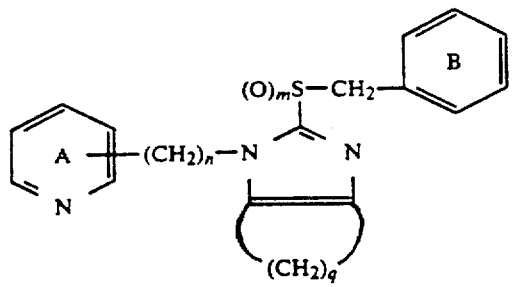

Signed and Sealed this

Ninth Day of March, 1993

Attest:

STEPHEN G. KUNIN

Attesting Officer  Acting Commissioner of Patents and Trademarks